United States Patent
Wu et al.

(10) Patent No.: US 9,481,714 B2
(45) Date of Patent: Nov. 1, 2016

(54) FUSION PROTEINS FOR USE AS IMMUNOGENIC ENHANCERS FOR INDUCING ANTIGEN-SPECIFIC T CELL RESPONSES

(71) Applicant: TheVax Genetics Vaccine Co., Ltd., Taipei (TW)

(72) Inventors: Chia-Mao Wu, Hsinchu County (TW); Hsiu-Kang Chang, Taipei (TW)

(73) Assignee: TheVax Genetics Vaccine Co., Ltd., Taipei (TW)

(*) Notice: Subject to any disclaimer, the term of this patent is extended or adjusted under 35 U.S.C. 154(b) by 94 days.

(21) Appl. No.: 14/095,760

(22) Filed: Dec. 3, 2013

(65) Prior Publication Data

US 2014/0154285 A1 Jun. 5, 2014

Related U.S. Application Data

(60) Provisional application No. 61/733,879, filed on Dec. 5, 2012.

(51) Int. Cl.
*A61K 39/00* (2006.01)
*C07K 14/005* (2006.01)
(Continued)

(52) U.S. Cl.
CPC .............. *C07K 14/005* (2013.01); *A61K 39/12* (2013.01); *A61K 39/135* (2013.01); *A61K 39/17* (2013.01); *A61K 39/21* (2013.01); *A61K 39/385* (2013.01); *A61K 47/4833* (2013.01); *C07K 14/70596* (2013.01); *C07K 14/81* (2013.01); *C12N 9/1077* (2013.01); *C12N 9/14* (2013.01);
(Continued)

(58) Field of Classification Search
None
See application file for complete search history.

(56) References Cited

U.S. PATENT DOCUMENTS 5,686,281 A * 11/1997 Roberts .................. 435/456
7,314,632 B1 1/2008 Fitzgerald
(Continued)

FOREIGN PATENT DOCUMENTS

EP 2078726 A1 * 7/2009
WO WO 94 02610 * 2/1994
(Continued)

OTHER PUBLICATIONS

Ahn et al., CD28 isoform 2 [Bos taurus], Accession No. AAL40878.1 (2002).*
(Continued)

*Primary Examiner* — Janet L Andres
*Assistant Examiner* — M. Franco Salvoza
(74) *Attorney, Agent, or Firm* — Hsiu-Ming Saunders; Intellectual Property Connections, Inc.

(57) ABSTRACT

A fusion protein for use as an immunogen enhancer for enhancing antigen-specific T cell responses is disclosed. The fusion protein comprises: (a) an antigen-presenting cell (APC)-binding domain or a CD91 receptor-binding domain; (b) a protein transduction domain; and (c) an antigen of a pathogen, wherein the APC-binding domain or the CD91 receptor-binding domain is located at the N-terminus of the fusion protein, and the antigen of the pathogen is located at the C-terminus of the protein transduction domain. The protein transduction domain is selected from the group consisting of: (i) a fusion polypeptide, comprising a T cell sensitizing signal-transducing peptide, a linker, and a translocation peptide; (ii) a T cell-sensitizing signal-transducing peptide; and (iii) a translocation peptide of 34-112 amino acid residues in length.

15 Claims, 10 Drawing Sheets

(51) Int. Cl.
| | |
|---|---|
| *A61K 39/21* | (2006.01) |
| *A61K 47/48* | (2006.01) |
| *A61K 39/385* | (2006.01) |
| *C07K 14/705* | (2006.01) |
| *A61K 39/12* | (2006.01) |
| *A61K 39/135* | (2006.01) |
| *A61K 39/17* | (2006.01) |
| *C07K 14/81* | (2006.01) |
| *C12N 9/10* | (2006.01) |
| *C12N 9/14* | (2006.01) |
| *C07K 14/21* | (2006.01) |

(52) U.S. Cl.
CPC .... *A61K 2039/57* (2013.01); *A61K 2039/585* (2013.01); *A61K 2039/6031* (2013.01); *C07K 14/21* (2013.01); *C07K 2319/02* (2013.01); *C07K 2319/04* (2013.01); *C07K 2319/095* (2013.01); *C07K 2319/33* (2013.01); *C07K 2319/40* (2013.01); *C07K 2319/55* (2013.01); *C12N 2710/20034* (2013.01); *C12N 2750/10034* (2013.01); *C12N 2760/18134* (2013.01); *C12N 2770/24334* (2013.01); *C12N 2770/32134* (2013.01); *C12Y 204/02036* (2013.01); *C12Y 306/05002* (2013.01)

(56) References Cited

U.S. PATENT DOCUMENTS

| | | | |
|---|---|---|---|
| 7,335,361 | B2 | 2/2008 | Liao et al. |
| 7,378,100 | B2 | 5/2008 | Chang et al. |
| 7,465,455 | B2 | 12/2008 | Chang et al. |
| 2009/0155297 | A1* | 6/2009 | Mrsny .................. 424/192.1 |

FOREIGN PATENT DOCUMENTS

| | | | |
|---|---|---|---|
| WO | WO 2004087196 | A2 * | 10/2004 |
| WO | WO 2008036682 | A2 * | 3/2008 |
| WO | WO 2011161260 | A1 * | 12/2011 |

OTHER PUBLICATIONS

D. Craig Hooper et al. "Rabies ribonucleocapsid as an oral immunogen and immunological enhancer" Proc. Natl. Acad. Sci. USA, vol. 91, pp. 10908-10912. Nov. 1994, Immunology.

Derek T O'Hagan,"New Generation Vaccine" Adjuvants Encyclopedia of Life Sciences & 2007. John Wiley & Sons, Ltd., pp 1-7.

* cited by examiner

1: RAP1-PE268-313-E7-K3
2: PE407-E7-K3
M: Molecular weight marker

Lane 1, 4: Molecular weight marker
Lane 2: RAP1-CD28convPE1-E7-K3 (mouse CD28conv, reduced)
Lane 3: RAP1-CD28convPE1-E7-K3 (mouse CD28conv, non-reduced)
Lane 5: RAP1-CD28convPE1-E7-K3 (human CD28conv, reduced)
Lane 6: RAP1-CD28convPE1-E7-K3 (human CD28conv, non-reduced)

FIG. 10

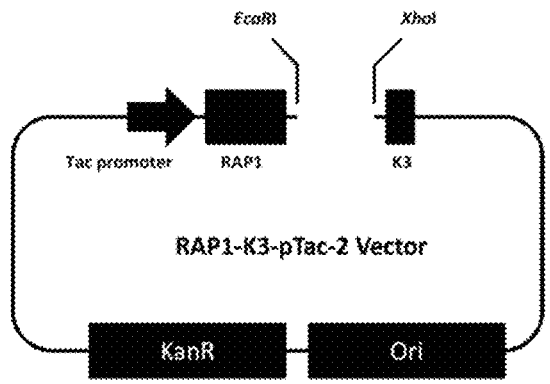

FIG. 11

| | | | | | |
|---|---|---|---|---|---|
| 1. PE$_{268\text{-}313}$-E7 | | EcoRI | Linker | PE | HPV16 E7 | XhoI |
| 2. CD28convPE$_t$-E7 | | EcoRI | CD28 epitope | PE | HPV16 E7 | XhoI |
| 3. CD28convPE$_t$-E7$_{18}$ | | EcoRI | CD28 epitope | PE | HPV18 E7 | XhoI |
| 4. HCVcore | | | | EcoRI | HCV core protein | XhoI |
| 5. CD28convPE$_t$-HCVcore | EcoRI | CD28 epitope | PE | HCV core protein | XhoI |
| 6. CD28conv-HCVcore | | EcoRI | CD28 epitope | HCV core protein | XhoI |
| 7. HBx | | | | EcoRI | HBV X protein | XhoI |
| 8. CD28convPE$_t$-HBx | EcoRI | CD28 epitope | PE | HBV X protein | XhoI |
| 9. CD28conv-HBx | | EcoRI | CD28 epitope | HBV X protein | XhoI |
| 10. HBx$_{stop}$ | | | | EcoRI | HBV X protein stop | XhoI |
| 11. CD28convPEt-HBx$_{stop}$ | EcoRI | CD28 epitope | PE | HBV X protein stop | XhoI |
| 12. CD28conv-HBx$_{stop}$ | | EcoRI | CD28 epitope | HBV X protein stop | XhoI |
| 13. PCV2$_{ORF2}$ | | | | EcoRI | PCV2$_{ORF2}$ | XhoI |
| 14. PE$_{268\text{-}313}$-PCV2$_{ORF2}$ | EcoRI | Linker | PE | PCV2$_{ORF2}$ | XhoI |
| 15. CD28convPE$_t$-PCV2$_{ORF2}$ | EcoRI | CD28 epitope | PE | PCV2$_{ORF2}$ | XhoI |
| 16. PE$_{268\text{-}313}$-DGD | | EcoRI | Linker | PE | PRRSV ORF7$_{64\text{-}123}$ | XhoI |
| 17. CD28convPE$_t$-DGD | EcoRI | CD28 epitope | PE | PRRSV ORF7$_{64\text{-}123}$ | XhoI |
| 18. PE$_{268\text{-}313}$-M12 | | EcoRI | Linker | PE | PRRSV ORF1b$_{1046\text{-}1210}$ | XhoI |
| 19. CD28convPE$_t$-M12 | EcoRI | CD28 epitope | PE | PRRSV ORF1b$_{1046\text{-}1210}$ | XhoI |
| 20. PE$_{268\text{-}313}$-PQAB | | EcoRI | Linker | PE | American strain: ORF6$_{2\text{-}26}$+ORF5$_{31\text{-}63}$ | XhoI |
| 21. CD28convPE$_t$-PQAB | EcoRI | CD28 epitope | PE | American strain: ORF6$_{2\text{-}26}$+ORF5$_{31\text{-}63}$ | XhoI |
| 22. PE$_{268\text{-}313}$-RSAB | | EcoRI | Linker | PE | European strain: ORF6$_{2\text{-}28}$+ORF5$_{31\text{-}64}$ | XhoI |
| 23. CD28convPE$_t$-RSAB | EcoRI | CD28 epitope | PE | European strain: ORF6$_{2\text{-}28}$+ORF5$_{31\text{-}64}$ | XhoI |

FIG. 13A

| Group | Sub-group | Vaccine | Protein absorbent | μg/dose |
|---|---|---|---|---|
| HPV16 E7 | A | Placebo | Aluminum Phosphate | - |
|  | B | $PE_{407}$-K3 | Aluminum Phosphate | 100 |
|  | C | $PE_{407}$-E7-K3 | Aluminum Phosphate | 100 |
|  | D | RAP1-K3 | Aluminum Phosphate | 100 |
|  | E | RAP1-CD28convPE$_t$-E7-K3 | Aluminum Phosphate | 100 |
| HPV18 E7 | A | Placebo | Aluminum Phosphate | - |
|  | B | RAP1-K3 | Aluminum Phosphate | 100 |
|  | C | RAP1-CD28convPE$_t$-E7$_{18}$-K3 | Aluminum Phosphate | 100 |
| HCV core | A | Placebo | Aluminum Phosphate | - |
|  | B | RAP1-K3 | Aluminum Phosphate | 200 |
|  | C | RAP1-HCVcore-K3 | Aluminum Phosphate | 200 |
|  | D | RAP1-CD28conv-HCVcore-K3 | Aluminum Phosphate | 200 |
|  | E | RAP1-CD28convPE$_t$-HCVcore-K3 | Aluminum Phosphate | 200 |
| HBV HBx | A | Placebo | Aluminum Phosphate | - |
|  | B | RAP1-HBx | Aluminum Phosphate | 100 |
|  | C | RAP1-HBx-K3 | Aluminum Phosphate | 100 |
|  | D | RAP1-CD28conv-HBx | Aluminum Phosphate | 100 |
|  | E | RAP1-CD28conv-HBx-K3 | Aluminum Phosphate | 100 |
|  | F | RAP1-CD28convPE$_t$-HBx | Aluminum Phosphate | 100 |
|  | G | RAP1-CD28convPE$_t$-HBx-K3 | Aluminum Phosphate | 100 |
| PCV2 ORF2 | A | Placebo | Aluminum Phosphate | - |
|  | B | $PE_{407}$-PCV2-K3 | Aluminum Phosphate | 40 |
|  | C | RAP1-PCV2-K3 | Aluminum Phosphate | 40 |
|  | D | RAP1-$PE_{268-313}$-PCV2-K3 | Aluminum Phosphate | 40 |
|  | E | RAP1-CD28convPE$_t$-PCV2-K3 | Aluminum Phosphate | 40 |
| PRRSV antigen | A | Placebo | Aluminum Phosphate | - |
|  | B | $PE_{407}$-PRRSV-K3 $^a$ | Aluminum Phosphate | 30 |
|  | C | RAP1-$PE_{268-313}$-PRRSV-K3 $^b$ | Aluminum Phosphate | 30 |
|  | D | RAP1-CD28convPE$_t$-PRRSV-K3 $^c$ | Aluminum Phosphate | 30 | a. Each dose contains a mixture of $PE_{407}$-DGD-K3 (12 μg), $PE_{407}$-M12-K3 (6 μg), $PE_{407}$-PQAB-K3 (6 μg), and $PE_{407}$-RSAB-K3 (6 μg).
b. Each dose contains a mixture of RAP1-$PE_{268-313}$-DGD-K3 (12 μg), RAP1-$PE_{268-313}$-M12-K3 (6 μg), RAP1-$PE_{268-313}$-PQAB-K3 (6 μg), and RAP1-$PE_{268-313}$-RSAB-K3 (6 μg).
c. Each dose contains a mixture of RAP1-CD28convPE$_t$-DGD-K3 (12 μg), RAP1-CD28convPE$_t$-M12-K3 (6 μg), RAP1-CD28convPE$_t$-PQAB-K3 (6 μg), and RAP1-CD28convPE$_t$-RSAB-K3 (6 μg).

FIG. 13B

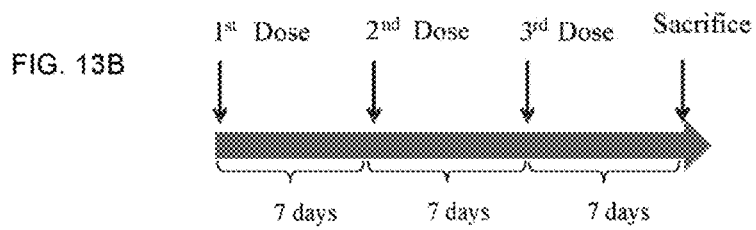

1st Dose, 2nd Dose, 3rd Dose, Sacrifice — 7 days, 7 days, 7 days

FIG. 14A

*Ex vivo* T Cell Immunogenicity (5 X 10⁵ splenocytes)

| Group | Vaccine | CD3+/CD4+/IFNr+ T cell counts Without E7 Antigen Stimulation | CD3+/CD4+/IFNr+ T cell counts With E7 Antigen Stimulation | CD3+/CD8+/IFNr+ T cell counts Without E7 Antigen Stimulation | CD3+/CD8+/IFNr+ T cell counts With E7 Antigen Stimulation |
|---|---|---|---|---|---|
| A | Placebo | 13 | 14 | 24 | 33 |
| B | PE$_{407}$-K3 | 21 | 26 | 16 | 25 |
| C | PE$_{407}$-E7-K3 | 18 | 40 | 29 | 34 |
| D | RAP1-K3 | 8 | 17 | 26 | 28 |
| E | RAP1-CD28convPE$_t$-E7-K3 | 10 | 198 | 20 | 233 |

FIG. 14B

*Ex vivo* T Cell Immunogenicity (1.5 X 10⁶ splenocytes)

| Group | Vaccine | CD3+/CD4+/IFNr+ Without E7$_{49}$ Antigen Stimulation | CD3+/CD4+/IFNr+ With E7$_{49}$ Antigen Stimulation | CD3+/CD8+/IFNr+ Without E7$_{49}$ Antigen Stimulation | CD3+/CD8+/IFNr+ With E7$_{49}$ Antigen Stimulation |
|---|---|---|---|---|---|
| A | Placebo | 2 | 6 | 2 | 0 |
| B | RAP1-K3 | 2 | 12 | 5 | 36 |
| C | RAP1-CD28convPE$_t$-E7$_{49}$-K3 | 12 | 614 | 49 | 328 |

FIG. 14C

*Ex vivo* T Cell Immunogenicity (1.5 X 10⁶ splenocytes)

| Group | Vaccine | CD3+/CD4+/IFNr+ Without HCVcore Antigen Stimulation | CD3+/CD4+/IFNr+ With HCVcore Antigen Stimulation | CD3+/CD8+/IFNr+ Without HCVcore Antigen Stimulation | CD3+/CD8+/IFNr+ With HCVcore Antigen Stimulation |
|---|---|---|---|---|---|
| A | Placebo | 13 | 8 | 24 | 34 |
| B | RAP1-K3 | 8 | 46 | 26 | 33 |
| C | RAP1-HCVcore-K3 | 13 | 100 | 15 | 54 |
| D | RAP1-CD28conv-HCVcore-K3 | 11 | 158 | 18 | 260 |
| E | RAP1-CD28convPEt-HCVcore-K3 | 13 | 236 | 23 | 521 |

FIG. 14D

*Ex vivo* T Cell Immunogenicity (5 X 10⁵ splenocytes)

| Group | Vaccine | CD3+/CD4+/IFNr+ Without HBx Antigen Stimulation | CD3+/CD4+/IFNr+ With HBx Antigen Stimulation | CD3+/CD8+/IFNr+ Without HBx Antigen Stimulation | CD3+/CD8+/IFNr+ With HBx Antigen Stimulation |
|---|---|---|---|---|---|
| A | Placebo | 3 | 5 | 1 | 1 |
| B | RAP1-HBx | 6 | 18 | 3 | 9 |
| C | RAP1-HBx-K3 | 2 | 10 | 6 | 4 |
| D | RAP1-CD28conv-HBx | 1 | 23 | 6 | 8 |
| E | RAP1-CD28conv-HBx-K3 | 9 | 18 | 1 | 18 |
| F | RAP1-CD28convPEt-HBx | 4 | 34 | 4 | 74 |
| G | RAP1-CD28convPEt-HBx-K3 | 2 | 191 | 0 | 120 |

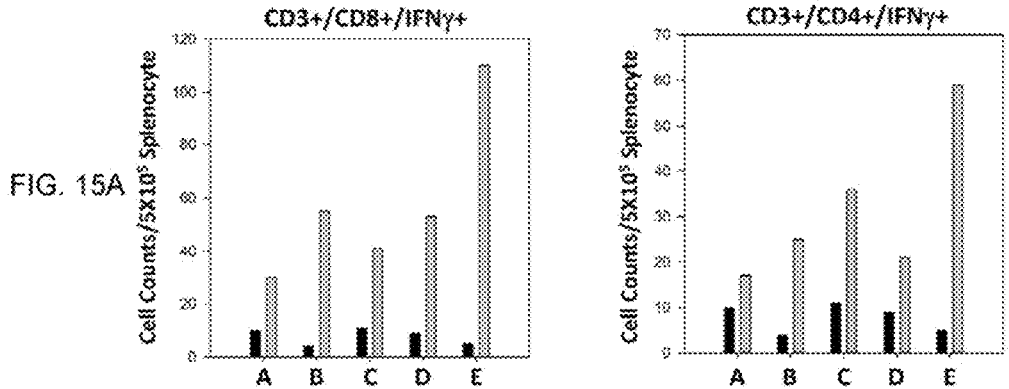
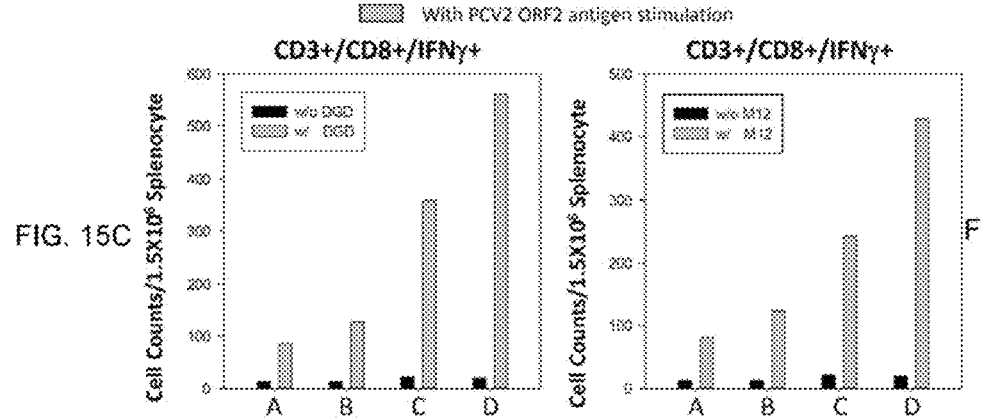
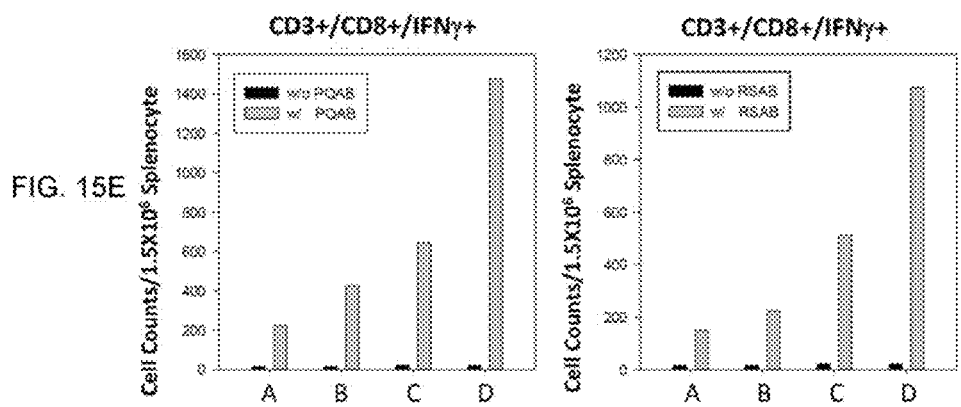
FIG. 15A
FIG. 15B
FIG. 15C
FIG. 15D
FIG. 15E
FIG. 15F

FUSION PROTEINS FOR USE AS IMMUNOGENIC ENHANCERS FOR INDUCING ANTIGEN-SPECIFIC T CELL RESPONSES

REFERENCE TO RELATED APPLICATION

The present application claims the priority to U.S. Provisional Application Ser. No. 61/733,879, filed Dec. 5, 2012, which is herein incorporated by reference in its entirety.

FIELD OF THE INVENTION

The present invention relates generally to fusion proteins, and more specifically to fusion proteins for enhancing T cell-mediated immune response.

BACKGROUND OF THE INVENTION

Molecular biology has enabled the production of subunit vaccines, in which the immunogen is a fragment or subunit of a parent protein or complex. The development of a stable vaccine that could elicit T cell sensitizing responses, and be flexible enough to incorporate sequences from many strains of an infectious agent would be desirable.

SUMMARY OF THE INVENTION

In one aspect, the invention relates to a fusion protein comprising:
(a) an antigen-presenting cell (APC)-binding domain or a CD91 receptor-binding domain, located at the N-terminus of the fusion protein;
(b) a protein transduction domain, located at the C-terminus of the APC-binding domain or the CD91 receptor-binding domain, the protein transduction domain being selected from the group consisting of:
  (i) a fusion polypeptide, comprising a T cell sensitizing signal-transducing peptide, a linker, and a translocation peptide, wherein:
    (1) the T cell sensitizing signal-transducing peptide is located at the N-terminus of the fusion polypeptide;
    (2) the linker comprises SEQ ID NO: 15, linking the T cell sensitizing signal-transducing peptide and the translocation peptide; and
    (3) the translocation peptide has 34-112 amino acid residues in length and comprises the amino acid sequence that is at least 90% identical to SEQ ID NO: 3, 20 or 4;
    (4) a T cell-sensitizing signal-transducing peptide; and
  (iii) a translocation peptide of 34-112 amino acid residues in length, comprising the amino acid sequence that is at least 90% identical to SEQ ID NO: 3, 20 or 4; and (c) an antigen of a pathogen, located at the C-terminus of the protein transduction domain; wherein:

the T cell-sensitizing signal-transducing peptide has 28-53 amino acid residues in length and comprises an amino acid sequence that is at least 90% identical to SEQ ID NO: 31, in which $Xaa^8$ is I or L; $Xaa^{10}$ is V, F or A, $Xaa^{11}$ is M or L, $Xaa^{17}$ is L or I; and the APC-binding domain or the CD91 receptor-binding domain is free of the amino acid sequence of *Pseudomonas* exotoxin A (PE) binding domain I if the protein transduction domain is the translocation peptide (biii).

In one embodiment of the invention, the APC-binding domain or the CD91 receptor-binding domain is a polypeptide comprising an amino acid sequence that is at least 90% identical to the sequence selected from the group consisting of SEQ ID NOs: 5, 9, 6, 7, and 8. Alternatively, the APC-binding domain is selected from the group consisting of receptor-associated protein-1 (RAP1) domain III, alpha-2-macroglobulin receptor-associated protein (A2M) HIV-Tat, and heat shock proteins (HSPs), and *Pseudomonas* exotoxin A (PE) binding domain I.

In another embodiment of the invention, the fusion protein is free of the amino acid sequence of *Pseudomonas* exotoxin A (PE) binding domain I.

In another embodiment of the invention, the fusion protein further comprises an endoplasmic reticulum retention sequence located at the C-terminus of the fusion protein.

In another embodiment of the invention, the endoplasmic reticulum retention sequence comprises the amino acid sequence of Lys-Asp-Glu-Leu (SEQ ID NO: 14). The ER retention sequence may comprise a sequence selected from the group consisting of SEQ ID NOs: 14, 16-19. Alternatively, the ER retention sequence may consist of a sequence selected from the group consisting of SEQ ID NOs: 16-19.

In another embodiment of the invention, the fusion protein is free of an endoplasmic reticulum retention sequence at C-terminus thereof if the antigen contains 10 or more epitopes.

In another embodiment of the invention, the protein transduction domain is the fusion polypeptide (bi).

In another embodiment of the invention, the protein transduction domain is the T cell-sensitizing signal-transducing peptide (bii).

In another embodiment of the invention, the fusion protein further comprises an additional linker between the protein transduction domain and the antigen, the additional linker comprising SEQ ID NO: 15.

In another embodiment of the invention, the protein transduction domain is the translocation peptide (biii).

In another embodiment of the invention, the fusion protein further comprises an additional linker between the APC-binding domain or the CD91 receptor-binding domain and the translocation peptide, the additional linker comprising SEQ ID NO: 15.

In another embodiment of the invention, the protein transduction domain comprises the sequence of SEQ ID NO: 30.

In another embodiment of the invention, the APC-binding domain comprises an amino acid sequence that is at least 95% identical to the sequence selected from the group consisting of SEQ ID NOs: 5, 9, 6, 7, and 8.

In another embodiment of the invention, the APC-binding domain or the CD91 receptor-binding domain is a polypeptide comprising an amino acid sequence selected from the group consisting of SEQ ID NOs: 5, 9, 6, 7, and 8.

In another embodiment of the invention, the T cell sensitizing signal-transducing peptide comprises an amino acid sequence that is at least 90% identical to SEQ ID NO: 1 or 2.

In another embodiment of the invention, the T cell sensitizing signal-transducing peptide comprises an amino acid sequence selected from the group consisting of SEQ ID NO: 1 and 2.

In another embodiment of the invention, the translocation peptide comprises an amino acid sequence selected from the group consisting of SEQ ID NO: 3, 20, and 4.

In another embodiment of the invention, the translocation peptide has 34-61 amino acid residues in length.

In another embodiment of the invention, the protein transduction domain of the fusion protein as aforementioned possesses the following features: (i) the T cell-sensitizing signal-transducing peptide comprises the amino acid sequence of SEQ ID NO: 1 or 2, and (ii) the translocation peptide comprises the amino acid sequence that is at least 95% identical to SEQ ID NO: 3.

The T cell sensitizing signal-transducing peptide exhibits a characteristic of eliciting an antibody that recognizes and binds to the amino acid sequence of $K^1(X)^2E^3(X)^4(X)^5 Y^6P^7P^8P^9Y^{10}$ (SEQ ID NO: 32) of CD28 receptor on T cells, wherein $(X)^2$ is I or L; $(X)^4$ is V, F or A, and $(X)^5$ is M or L.

In another aspect, the invention relates to a fusion protein consisting of:
(a) an antigen-presenting cell (APC)-binding domain or a CD91 receptor-binding domain, located at the N-terminus of the fusion protein;
(b) a protein transduction domain, located at the C-terminus of the APC-binding domain or the CD91 receptor-binding domain, the protein transduction domain being selected from the group consisting of:
  (i) a fusion polypeptide, comprising a T cell sensitizing signal-transducing peptide, a linker, and a translocation peptide, wherein:
    (1) the T cell sensitizing signal-transducing peptide is located at the N-terminus of the fusion polypeptide;
    (2) the linker comprises SEQ ID NO: 15, linking the T cell sensitizing signal-transducing peptide and the translocation peptide; and
    (3) the translocation peptide has 34-112 amino acid residues in length and comprises the amino acid sequence that is at least 90% identical to SEQ ID NO: 3, 20 or 4;
  (ii) a T cell-sensitizing signal-transducing peptide; and
  (iii) a translocation peptide of 34-112 amino acid residues in length, comprising the amino acid sequence that is at least 90% identical to SEQ ID NO: 3, 20 or 4; and
(c) an antigen of a pathogen, located at the C-terminus of the protein transduction domain; wherein:
the T cell-sensitizing signal-transducing peptide has 28-53 amino acid residues in length and comprises an amino acid sequence that is at least 90% identical to SEQ ID NO: 31, in which $Xaa^8$ is I or L; $Xaa^{10}$ is V or A, $Xaa^{11}$ is M or L, $Xaa^{17}$ is L or I; and
the APC-binding domain or the CD91 receptor-binding domain is free of the amino acid sequence of *Pseudomonas* exotoxin A (PE) binding domain I if the protein transduction domain is the translocation peptide (biii).

The antigen-presenting cell (APC) may be selected from the group consisting of dendritic cells, macrophages, B-cells and monocytes.

In one embodiment of the invention, the cell membrane of the APC comprises a CD91 receptor.

In another aspect, the invention relates to a vaccine composition comprising: (a) a therapeutically effective amount of a fusion protein as aforementioned; and (b) an adjuvant.

The adjuvant is either an antigen delivery agent or an immune potentiator. In one embodiment of the invention, the vaccine composition comprises an antigen delivery agent and is free of an immune potentiator.

Further in another aspect, the invention relates to a method for inducing enhanced pathogen antigen-specific T cell responses, comprising: administering a vaccine composition comprising a therapeutically effective amount of a fusion protein as aforementioned to a subject in need thereof, and thereby inducing enhanced pathogen antigen-specific T cell responses.

Further in another aspect, the invention relates to a method for killing a disease cell that presents an antigen via class I MHC molecules on the cell membrane of the disease cell, comprising: administering a vaccine composition comprising a therapeutically effective amount of a fusion protein as aforementioned to a subject in need thereof, and thereby killing the disease cell that that presents the antigen via class I MHC molecules on the cell membrane of the disease cell.

In one embodiment of the invention, the disease cell is a cancer cell.

Yet in another aspect the invention relates to a method for preventing, treating infection caused by a pathogen, and/or minimizing symptoms caused by the infection, comprising: administering a vaccine composition comprising a therapeutically effective amount of the fusion protein as aforementioned to a subject in need thereof, and thereby preventing, treating infection caused by the pathogen, and/or minimizing symptoms caused by the infection.

The pathogen may be at least one selected from the group consisting of Human Papillomavirus (HPV), Porcine Reproductive and Respiratory Syndrome Virus (PRRSV), Human Immuno-deficient Virus (HIV-1), flu virus, dengue virus, Hepatitis C virus (HCV), Hepatitis B virus (HEW) and Porcine Circovirus 2 (PCV2).

In one embodiment of the invention, the fusion protein as aforementioned is for use in enhancing an antigen-specific cytotoxic T cell response in a subject in need thereof. The fusion protein may also be for use in enhancing an antigen-specific CD4+ T cell response, or for use as an immunogenic enhancer for inducing an enhanced antigen-specific antibody titer response, in a subject in need thereof.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 10 is a schematic drawing showing a RAP1-containing vector used for generating a plasmid containing a DNA insert from a pathogen.

FIG. 11 are schematic drawings illustrating constructions of fusion proteins containing antigens of various pathogens.

FIGS. 13A-B show animal groups, vaccines and dosage used for immunizing the animals, and immunization schedules.

FIGS. 14A-D are tables showing the results of ex vivo antigen-specific immune response analyses of CD3+/CD4+ splenocytes and CD3+/CD8+ splenocytes from the animal groups of FIG. 13A vaccinated with placebo or a fusion protein containing $E7_{16}$, $E7_{18}$, HCVcore, or HBx antigen.

FIGS. 15A-J show IFNγ+ cell counts in ex vivo antigen-specific immune response analyses of CD3+/CD8+ splenocytes and CD3+/CD4+ splenocytes from the animal groups of FIG. 13A vaccinated with placebo or a fusion protein containing a PCV2 (15A-B) or PRRSV antigen (15C-J).

DETAILED DESCRIPTION OF THE INVENTION

Figure 1:
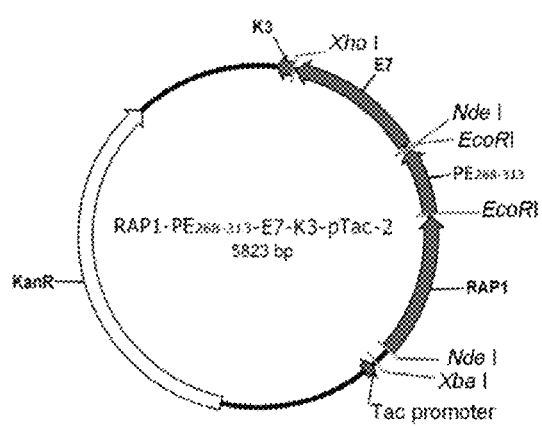
FIG. 1 is a vector map.
Figure 3:
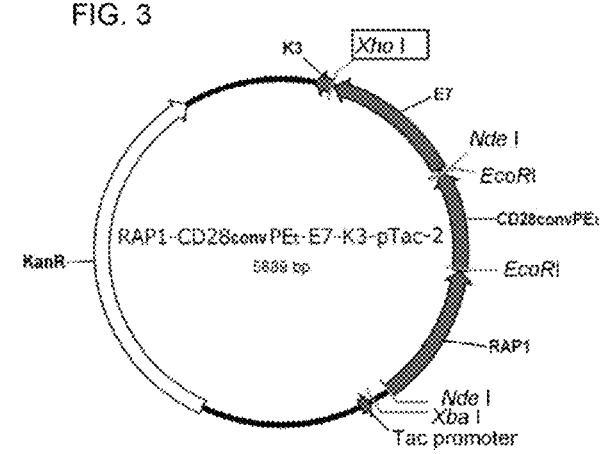
FIG. 3 is a vector map.
Figure 4:
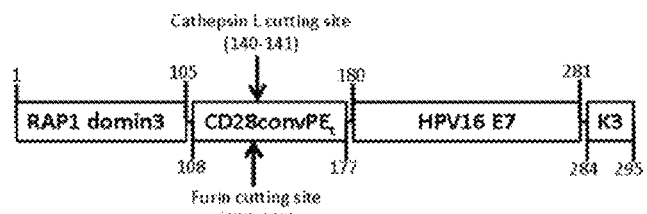
FIG. 4 is a schematic drawing illustrating one embodiment of the invention.

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "an antigen-presenting cell (APC) or accessory cell" refers to a cell that displays foreign antigens complexed with major histocompatibility complexes (MHC's) on their surfaces. T-cells may recognize these complexes using their T-cell receptors (TCRs). These cells process antigens and present them to T-cells. Main types of professional antigen-presenting cell: dendritic cells (DCs), macrophages, monocytes, and certain B-cells.

The term "an antigen-presenting cell (APC)-binding domain" refers to a domain that can bind to an antigen-presenting cell (APC). The APC-binding domain may be a polypeptide comprising an amino acid sequence that is at least 90% identical to the sequence selected from the group consisting of SEQ ID NOs: 5, 6, 7, 8, and 9. An APC-binding domain is a ligand that recognizes and binds to a receptor on APC.

Cluster of differentiation 91 (CD91) is a protein that forms a receptor in the membrane of cells and is involved in receptor-mediated endocytosis.

The term "a protein transduction domain" refers to a polypeptide or a fusion polypeptide having a function to sensitize T-cells and thus enhance antigen-specific T cell responses, and/or to guide or direct an antigen toward (i.e., to target to) class I major histocompatibility complex (MHC-I) pathway (i.e., a cytotoxic T cell pathway) of antigen presentation.

The term "to sensitize T cells" generally means that CD8+ and CD4+ T cells are sensitized and as a result, CD8+ (CTL) and CD4+ T cell responses to an antigen challenge are enhanced. An antigen-specific cell mediated immune response is measured by quantifying the production of antigen-specific induced γ-interferon in response to an antigen. For example, without a sensitization signal (i.e., without the protein transduction domain), an antigen alone may induce weak or no cell mediated immune response at all, i.e., weak or no production of antigen-specific γ-interferon from CD8+ and CD4+ T cells, while in the presence of a sensitization signal (the protein transduction domain), the antigen may induce an enhanced cell mediated immune response. Thus, the function of a sensitization signal (the protein transduction domain) is to sensitize CD4+ and CD8+ T cells in a host so that when the host is later challenged by an antigen, the antigen can induce an enhanced antigen-specific cell mediated immune response due to prior CD4+ and CD8+ T cell sensitization.

A protein transduction domain may be a peptide and/or polypeptide selected from the group consisting of:

(i) a fusion polypeptide, comprising a T cell sensitizing signal-transducing peptide, a linker, and a translocation peptide, wherein:
  (1) the T cell sensitizing signal-transducing peptide is located at the N-terminus of the fusion polypeptide;
  (2) the linker comprises SEQ ID NO: 15, linking the T cell sensitizing signal-transducing peptide and the translocation peptide; and
  (3) the translocation peptide has 34-112 amino acid residues in length and comprises the amino acid sequence that is at least 90% identical to SEQ ID NO: 3, 20 or 4;

(ii) a T cell-sensitizing signal-transducing peptide; and (iii) a translocation peptide of 34-112 amino acid residues in length, comprising the amino acid sequence that is at least 90% identical to SEQ ID NO: 3, 20 or 4.

A protein transduction domain may be "a fusion polypeptide", in which the fusion polypeptide comprises a T cell sensitizing signal-transducing peptide, a linker, and to translocation peptide. For example, the fusion polypeptide may be the polypeptide "CD28convPE$_t$".

The term "CD28conv" refers to a CD28 conserved region, which is a "T cell sensitizing signal-transducing peptide". It's an epitope for inducing CD28 agonist antibody.

The term "PE$_t$" or "PEt Core" refers to a RE translocation domain core with 34 amino acid residues in length.

A linker is present between the "CD28conv" and the "PE$_t$". The orientation or arrangement of the fusion polypeptide "CD28convPE$_t$" is important in that "CD28conv" (or the T cell sensitizing signal-transducing peptide) must be at the upstream to the PE$_t$ (or the translocation peptide), i.e., PE$_t$ must be at the C-terminus of the "CD28conv" to obtain enhanced T-cell responses. The "CD28convPE$_t$" can raise much higher IgG titer (called CD28-specific agonist antibody) specific to CD28conv than the reversed orientation fusion peptide PE$_t$CD28conv. The CD28-specific agonist antibody can sensitize both CD4+ and CD8+ T cells. The correct orientation fusion polypeptide CD28convPE$_t$ contains a linker (RXRXKR) between CD28conv and PE$_t$ domains. The linker contains an antigen presenting cell (APC)-specific protease (cathepsin L) cutting site Lys-Arg (KR). Therefore, the fusion protein RAP1-CD28convPE$_t$-Antigen-K3 can be digested into the two fragments: RAP1-CD28conv and PE$_t$-Antigen-K3. The RAP1-CD28conv fragment can be further digested in the lysosome and the epitope of CD28conv is then presented to the APC cell surface via MHC II pathway, which in turn elicits a humoral immune response producing CD28 agonist antibody. Thus, CD28 agonist antibody is produced by B cells. This CD28 agonist antibody can bind to CD28 on the T cell surface and pre-activate the T cells (CD4+ and CD8+ T cells).

A "T cell-sensitizing signal-transducing peptide" has 28-53 amino acid residues in length and comprises an amino acid sequence that is at least 90% identical to SEQ ID NO: 31, in which Xaa is I or L; Xaa$^{10}$ is V, F or A, Xaa$^{11}$ is M or L, Xaa$^{17}$ is L or I.

The T cell-sensitizing signal-transducing peptide comprises the critical region $K^1(I/L)^2E^3(V/P/A)^4(M/L)^5Y^6P^7P^5P^9Y^{10}$(SEQ ID NO: 32), wherein $(X)^2$ is I or L; $(X)^4$ is V, F or A, $(X)^5$ is M or L.

A T cell sensitizing signal-transducing peptide (TDIYCK-IEFMYPPPYLDNEKSNGTIIH; SEQ ID NO: 31, wherein $X^8$ is I, $X^{10}$ is F, $X^{11}$ is M) specific for mice was used in the following examples.

FIG. 7 is a schematic drawing illustrating the mechanisms of actions of T cell-sensitizing fusion proteins using the fusion protein RAP1-CD28convPE$_t$-E7-K3 as an example. RAP1-CD28convPE$_t$-E7-K3 comprises from N-terminus to the C-terminus: (1) the domain Ill of the full length RAP1 at the N-terminus. (2) CD28conv, (3) a linker, (4) a modified translocation peptide from *Pseudomonas* Exotoxin A, (5) a full length HPV type 16 E7 protein, and (6) the triple KDEL as an EIR retention signal at the C-terminus. The HPV16 E7 protein is processed into epitopes within the cells of a subject immunized with the fusion protein. The RAP1-CD28convPE$_t$-E7-K3 can elicit a better cytotoxic T-cell (CTL) response than the traditional vaccines that contain antigen only. RAP1-CD28convPE$_t$-E7-K3 protein was designed to improve APC (such as dendritic cell) uptake efficiency and enhance HPV16 E7 antigen processing toward a proteasome pathway, then presented via MHC I complexes. The mechanism of action of HPV16 E7 protein-specific CTL immune response elicited by the vaccine RAP1-CD28convPE$_t$-E7-K3 is illustrated in FIG. 7: (a) the vaccine binds to APC (such as dendritic cell) surface receptor (CD91) and internalized via endocytosis: (b1) RAP1-CD28convPE$_t$-E7-K3 undergoes proteolytic hydrolysis by cathepsin L protease digestion at the site before the translocation peptide PE$_t$; (b2) or recycles to the E.R. and undergoes proteolytic hydrolysis by furin protease at the site before the translocation peptide PE$_t$; (b3) At the meantime, RAP1-CD28conv was digested by lysosomal protease and the epitopes of CD28conv are then presented to the cell surface via MHC II and elicits CD28 agonist antibody production, which can pre-activate T cells; (c) The most important step is transmembrane translocation of the PE$_t$-E7-K3 into the cytoplasmic compartment from the lysosome by translocation peptide (PE); (d) the PE$_t$-E7-K3 undergoes digestion via proteasome pathway, then the epitopes of E7 are presented by MHC1 complex and elicit E7-specific cell mediated immune response.

FIG. 8 shows a sequence alignment of CD28 conserved regions from various species and the consensus sequence. The underlined sequence (KIEVMYPPPY; SEQ ID NO: 32, where $X^2$ is I, $X^4$ is V, $X^5$ is M) within the consensus sequence is a critical region for CD28 agonist antibody recognition and binding. This critical region sequence can be represented by $K^1(I/L)^2E^3(V/F/A)^4(M/L)^5Y^6P^7P^8P^9Y^{10}$, in which only the fourth amino acid residue therein is species-specific and should be V in human, rat, porcine, bovine, sheep, dog and horse; F in mouse, and V in turkey. The critical region sequence may be represented as $K^1(X)^2E^3(X)^4(X)^5Y^6P^7P^8P^9Y^{10}$ (SEQ ID NO: 32), wherein $(X)^2$ is I or L; $(X)^4$ is V, F or A, $(X)^5$ is M or L.

A PE translocation peptide may comprise the amino acid sequence that is at least 90% identical to SEQ ID NO: 3 or 20 For example, the amino acid sequence of a PE translocation peptide may be a.a. 280-a.a, 313 (SEQ ID NO: 3), a.a. 268-a.a 313 (SEQ ID NO: 20), a.a. 253-a.a. 313, or a.a. 253-a.a. 364 (SEQ ID NO: 4) of PE. That is, the amino acid sequence of a PE translocation peptide may contain any region of the PE domain II (a.a. 253 to a.a. 364; SEQ ID NO: 4) as long as it comprises a.a. 280-a.a. 313 (SEQ ID NO 3) essential fragment.

An antigen may be a pathogenic protein, polypeptide or peptide that is responsible for a disease caused by the pathogen, or is capable of inducing an immunological response in a host infected by the pathogen, or tumor-associated antigen (TAA) which is a polypeptide specifically expressed in tumor cells. The antigen may be selected from a pathogen or cancer cells including, but not limited to, Human Papillomavirus (HPV), PRRSV, HIV-1, flu virus, dengue virus, Hepatitis C virus (HCV), Hepatitis B virus (HBV), Porcine Circovirus 2 (PCV2), non-small cell lung cancer, breast carcinoma, melanoma, lymphomas, colon carcinoma, hepatocellular carcinoma and any combination thereof. For example, HPV E7 protein (E7), HCV core protein (HCV core), HBV X protein (HBx) were selected as antigens for vaccine development. The antigen may be a fusion antigen from a fusion of two or more antigens selected from one or more pathogenic proteins. For example, a fusion antigen of PRRSSV ORF6 and ORF5 fragments, or a fusion of antigenic proteins from PRRSV and PCV2 pathogens.

The function of an endoplasmic reticulum retention sequence is to assist translocation of an antigen from an endocytotic compartment into ER and retains it in the lumen. It comprises the sequence Lys Asp Glu Leu (KDEL) or RDEL. An ER sequence may comprise, or consists essentially of, or consist of, the sequence of KKDLRDELKDEL (SEQ ID NO: 16) KKDELRDELKDEL (SEQ ID NO: 17) KKDELRVELKDEL (SEQ ID NO: 18).

Receptor-associated protein (RAP1) with a molecular weight of 39 kDa is an ER resident protein and molecular chaperone for LDL receptor-related protein. It has a high binding affinity to CD91 (Kd~3 nM) and is composed by three functional-similar domains.

The invention relates to the discovery of induction and enhancement of T cell mediated immune responses by fusion proteins according to the invention. Using RAP1-CD28convPE$_t$-E7-K3 an example, the strategy of RAP1-CD28convPE$_t$-E7-K3 vaccine is focused primarily on stimulating the production and activation of T cells that can recognize HPV16 infected cells expressing the target antigen E7. By delivering antigens to dendritic cells, it can generate antigen-specific CD8+ T cells and CD4+ T cells. Type 1-helper CD4+ T cells particularly are able to efficiently stimulate and augment the immune response of cytotoxic CD8+ T cells. Together, these two arms of the adaptive immune system have the specificity and potency to kill HPV16-infected cells or HPV16-associated tumor cells at multiple sites in the body without inflicting significant damage on normal tissues.

The term "subject" refers to a human or a non-human animal.

The term "treating" or "treatment" refers to administration of an effective amount of the fusion protein to a subject in need thereof, who has cancer or infection, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "an effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

Abbreviations: CD 28, Cluster of Differentiation 28.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Constructions of Expression Vectors

FIG. 1 shows the expression vector for the fusion protein RAP1-PE$_{268-313}$-E7-K3, which comprises a RAP1 domain 3 (SEQ ID NO: 5), a translocation minimum essential peptide (PE$_{268-313}$; SEQ ID NO: 20), the antigen E7, and an endoplasmic reticulum retention sequence (K3, or a KDEL signal; SEQ ID NO: 16, 17, 18, or 19). The translocation minimum essential peptide (PE$_{268-313}$; SEQ ID NO: 20) was obtained from PE (SEQ ID NO: 10) polypeptide sequence region from a.a. 268 to a.a. 313.

This expression vector was constructed by using the plasmid RAP1-K3 shown in FIG. 10. The plasmid RAP1-K3 (FIG. 10), which contains a fusion gene of RAP-1 domain 3 and K3, was generated as follows: A DNA fragment encoding $^{NdeI}$RAP1-$^{(EcoRI,\ XhoI)}$-K3$^{XhoI}$ was synthesized by a PCR method and ligated into the plasmid pUC18 backbone with kanamycin resistance gene to obtain the plasmid RAP1-K3 (FIG. 10). To generate the expression vector RAP1-PE$_{268-313}$-E7-K3 (FIG. 1), a DNA fragment encoding PE$_{268-313}$-E7 was inserted into the plasmid RAP1-K3 (FIG. 10). Using similar methods, DNA fragments encoding various fusion peptides were generated by PCR (FIG. 11) and inserted, respectively, into the plasmid RAP1-K3 (FIG. 10) to generate expression vectors for various fusion proteins (FIGS. 12A-F). FIG. 3 illustrates the expression vector for the fusion protein RAP1-CD28convPE$_t$-E7-K3 (FIG. 3).

The fragment CD28convPE$_t$ contains cathepsin L and furin protease cutting sites. FIG. 4 shows an amino acid sequence map of the fusion protein RAP1-CD28convPE$_t$-E7-K3 to illustrate the importance of the fragment CD28convPE$_t$. The two arrows indicate cathepsin L and furin protease cutting sites, respectively. These two cutting sites not only serve as linkers to ligate CD28conv and PE$_t$-E7 but also allow cutting of the fusion protein to release the fragment PE$_t$-E7-K3 to the cytoplasm from the lysosome. Any other antigens of interest from various pathogens may replace E7 to fuse with CD28convPE$_t$ and the fusion product can then be inserted into the plasmid of FIG. 10 to make a variety of expression vectors for fusion proteins illustrated in FIG. 11.

The sequence of PE$_{268-313}$ is pletftrhrqprgweqleqcgypvqrlvalylaarlswnqvdqvir (SEQ ID NO: 20). The whole sequence of CD28convPE$_t$ is as follows: tdiyfckiefmy pppyldneksngtiihrarykrgweqleqcgypvqrlvalylaarlswnqvdqvirgs (SEQ ID NO: 30), the sequence underlined represents a linker sequence containing Cathepsin L and furin protease cutting sites.

Example 2

Protein Expression

E. coli BL21 cells harboring a protein expression vector were cultured in Luria Bertani broth containing 25 μg/ml kanamycin at 37° C. When the culture reached an early log phase, (A600=0.1 to 0.4), isopropyl-1-thio-β-D-galactopyranoside (IPTG) was added at a final concentration of 0.5 to 2 mM for induction. Cells were harvested after 4 hours IPTG induction and disrupted by sonication. The overexpressed protein-containing inclusion bodies were isolated and solubilized in 8M urea/TN buffer (8M urea, 50 mM Tris, 50 mM NaCl, pH 8.0).

Figure 2:
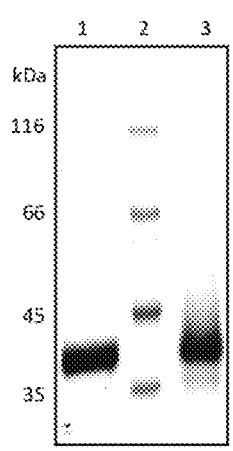
FIG. 2 is a photograph showing the result of SDS-PAGE analyses of fusion proteins.

The refolding of the fusion protein RAP1-$PE_{268-313}$-E7-K3 was performed by dialysis against 50× volume of TNZ buffer (50 mM Tris 50 mM NaCl and 0.01 mM $ZnCl_2$, pH 8.0) at 4° C. overnight. The refolded proteins were subject to SDS-PAGE analyses under reduced (with dithiothreitol; +DTT) and non-reduced (without dithiothreitol; −DTT) conditions (FIG. 2). The results indicated that most of the refolded proteins were monomers under a non-reduced condition, indicating that the RAP1 fusion protein refolded easily and were not aggregated (FIG. 2).

Figure 6A:
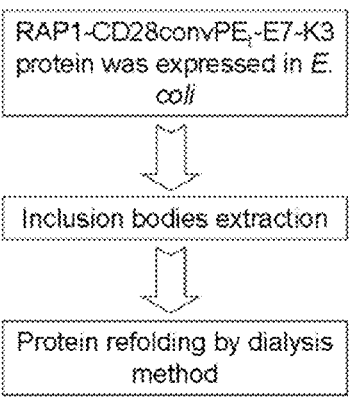
FIGS. 6A-B are a flow chart for preparation of fusion proteins and a photograph showing the result of SDS-PAGE analyses of fusion proteins, respectively.
Figure 6B:
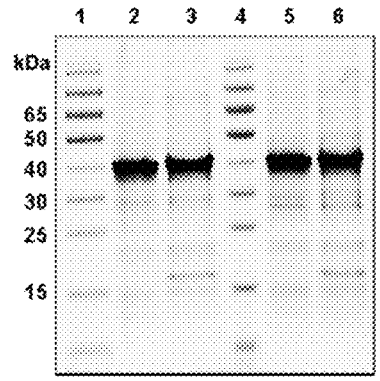
Figures 7, 8:
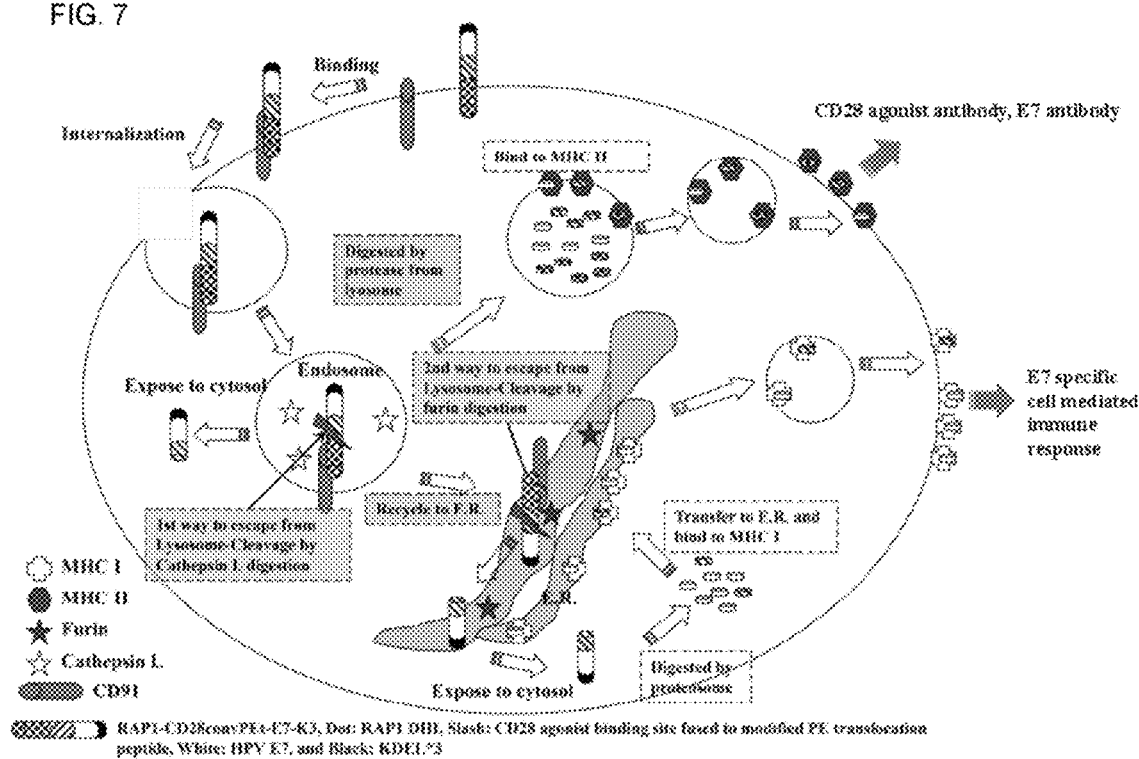
FIG. 7 is a schematic drawing illustrating the mechanisms of actions of T cell-sensitizing fusion proteins.
FIG. 8 shows sequence alignments of CD28 from various species: human (SEQ ID NO: 33), rat (SEQ ID NO: 34), mouse (SEQ ID NO: 35), rabbit (SEQ ID NO: 36), pig (SEQ ID NO: 37), bovine (SEQ ID NO: 38), sheep (SEQ ID NO: 39), dog (SEQ ID NO: 40), horse (SEQ ID NO: 41), turkey (SEQ ID NO: 42), and the consensus sequence SEQ ID NO: 43.

FIG. 6A is a flow chart illustrating that the fusion proteins RAP1-$CD28PE_t$E7-K3 (with mouse CD28conv or human CD28conv) were expressed and extracted from the inclusion bodies of E. coli cells). SDS-PAGE analyses indicated that the fusion proteins refolded well (FIG. 6B).

FIG. 11 illustrates a list of fusion proteins that were expressed using similar method described above: (1) RAP1-$PE_{268-313}$-E7-K3; (2) RAP1-CD28conv$PE_t$-E7-K3; (3) RAP1-CD28$PE_t$-$E7_{18}$K3; (4) RAP1-HCVcore-K3; (5) RAP1-CD28conv-HCVcore-K3; (6) RAP1-CD28conv$PE_t$-HCVcore-K3; (7) RAP1-HBx; (8) RAP1-HBx-K3; (9) RAP1-CD28conv-HBx; (10) RAP1-CD28conv-HBx-K3; (11) RAP1-CD28conv$PE_t$-HBx; (12) RAP1-CD28conv$PE_t$-HBx-K3; (13) RAP1-$PCV2_{ORF2}$-K3; (14) RAP1-$PE_{268-313}$-$PCV2_{ORF2}$-K3; (15) RAP1-CD28conv$PE_t$$PCV2_{ORF2}$-K3; (16) RAP1-$PE_{268-313}$-DGD-K3; (17) RAP1-$PE_{268-313}$-M12-K3; (18) RAP1-$PE_{268-313}$-PQAB-K3; (19) RAP1-$PE_{268-313}$-RSAB-K3; (20) RAP1-CD28conv$PE_t$-DGD-K3; (21) RAP1-CD28conv$PE_t$-M12-K3 (22) RAP1-CD28conv$PE_t$-PQAB-K3; (23) RAP1-CD28conv$PE_t$-RSAB-K3. These fusion proteins were refolded using the same method described above. The results of SDS-PAGE analyses indicated these fusion proteins al refolded well and were thus used for preparing vaccines (FIGS. 12A-F).

Example 3

Figure 5A:
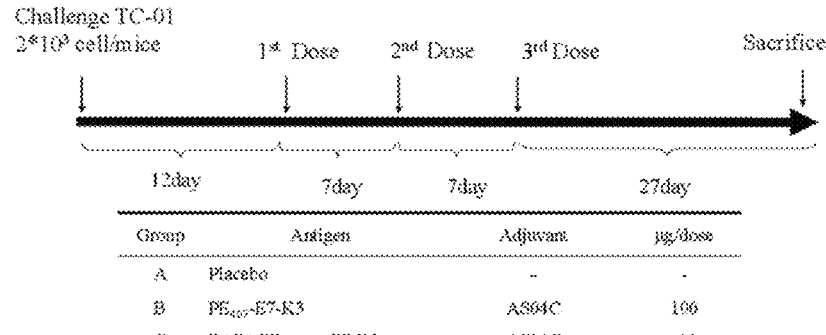
FIG. 5A shows immunization schedules.
Figure 5B:
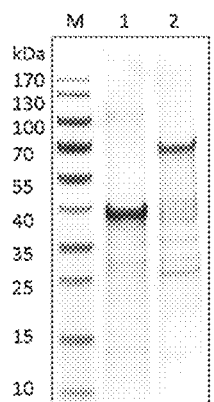
FIG. 5B is a photograph showing the result of SDS-PAGE analyses of fusion proteins.
Figure 5C:
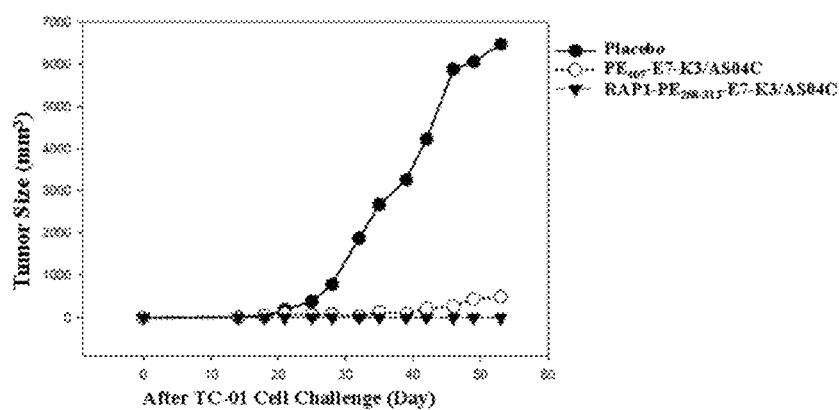
FIGS. 5C-D are graphs showing tumor size curves and percentage of tumor-free mice in the animal groups vaccinated with various fusion proteins or placebo, respectively.
Figure 5D:
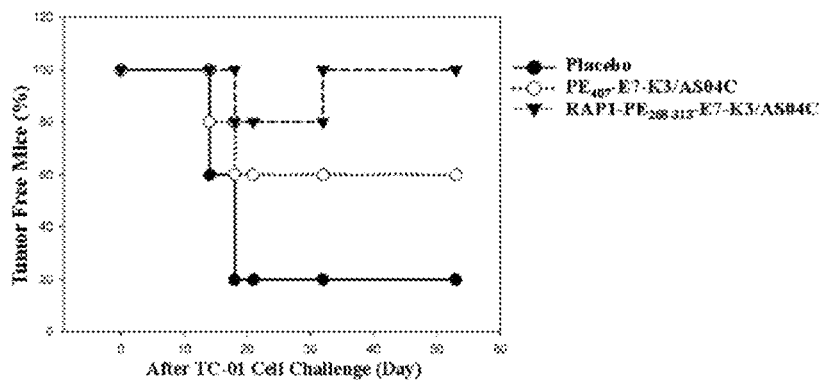

RAP1-$PE_{268-313}$-E7-K3 Inhibits Growth of Tumors Induced by Human Papilloma Virus (HPV) Type 16 E7 Protein The fusion proteins $PE_{407}$-E7-K3 and RAP1-$PE_{268-313}$-E7-K3 were expressed as described above and protein refolding examined by SDS-PAGE (FIG. 5B). Mice were challenged with $2\times10^3$ TC-01 cells (a mouse lung epithelia cell line harboring HPV type 16 E7 gene) via s.c. injection to induce HPV-16 type carcinoma. Twelve days after the TC-01 cell challenge, mice were vaccinated via s.c. with placebo (PBS+aluminum phosphate), PE407-E7-K3 (200 μg/dose) or RAP1-$PE_{268-313}$-E7-K3 (200 μg/dose) with AS04C (GlaxoSmithKline) as an adjuvant once per week for 3 weeks (FIG. 5A). AS04C, which is a cytotoxic T lymphocyte-enhancing adjuvant, comprises MPL (monophosphoryl lipid A, an immune potentiator) and aluminum phosphate (a protein absorbent for antigen delivery). The term "K3" stands for the amino acid sequence KDELKDELKDEL (SEQ ID NO: 19). The size of tumors and the number of tumor-free animals in each group were recorded (FIGS. 5C-D). The tumor growth was significantly suppressed by both vaccines $PE_{407}$-E7-K3 and RAP1-$PE_{268-313}$-E7-K3 with AS04C as an adjuvant. However, the mouse group vaccinated with RAP1-$PE_{268-313}$-E7-K3 had a higher rate of tumor-free mice. This indicated that the vaccine RAP1-$PE_{268-313}$-E7-K3 was as effective as or better than $PE_{407}$-E7-K3 in suppressing tumor growth, however was better in increasing the percentage of tumor-free animals.

Example 4

Figure 9A:
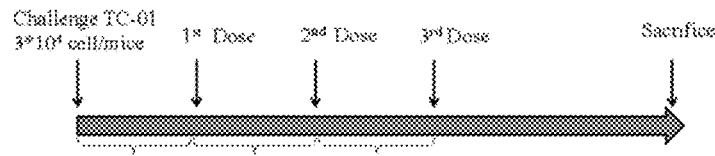
FIG. 9A shows immunization schedules.
Figure 9B:
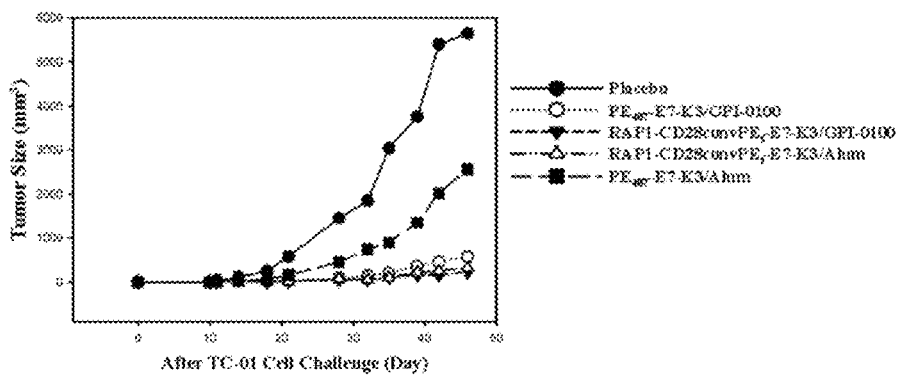
FIGS. 9B-C show tumor size curves and survival rate in the animal groups vaccinated with various fusion proteins or placebo, respectively.
Figure 9C:
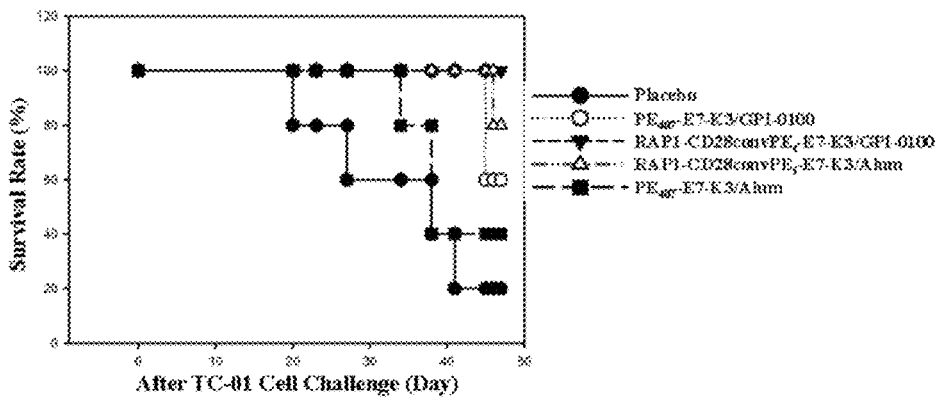
Figure 12A:
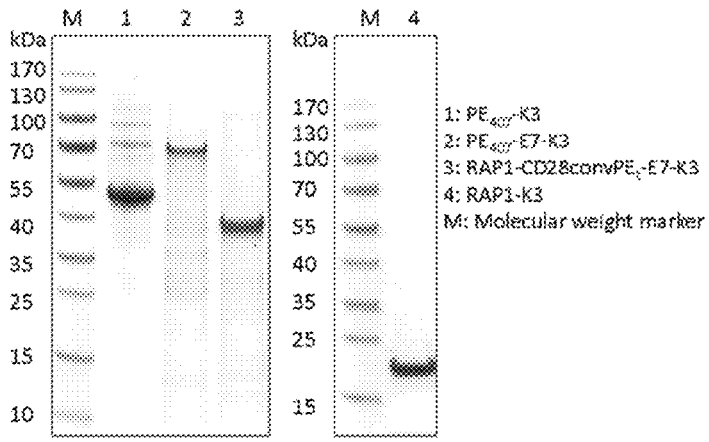
FIGS. 12A-F are photographs showing the results of SDS-PAGE analyses of various fusion proteins.
Figure 12B:
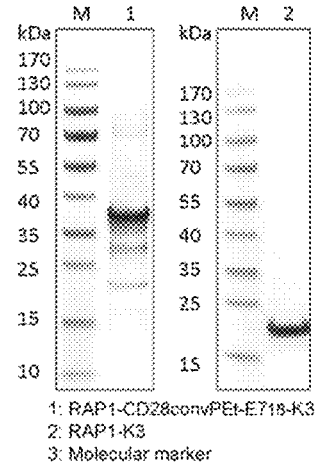
Figure 12C:
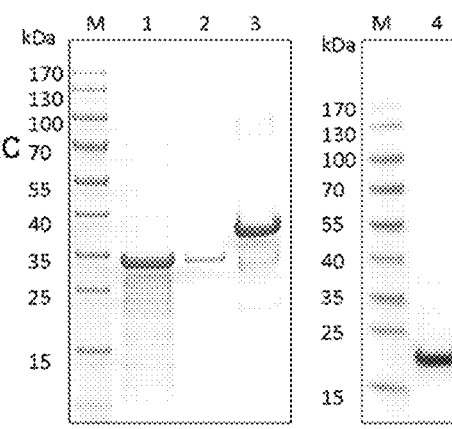
Figure 12D:
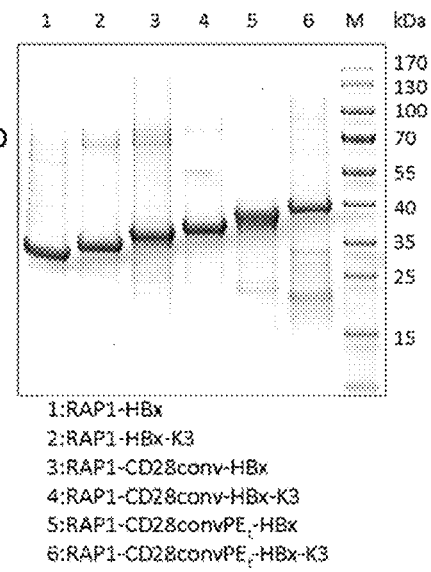
Figure 12E:
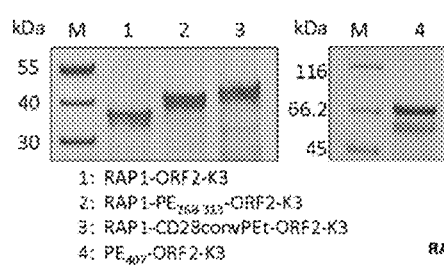
Figure 12F:
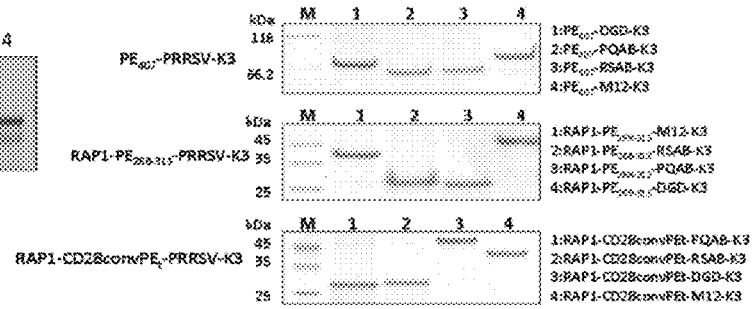
Figure 15G:
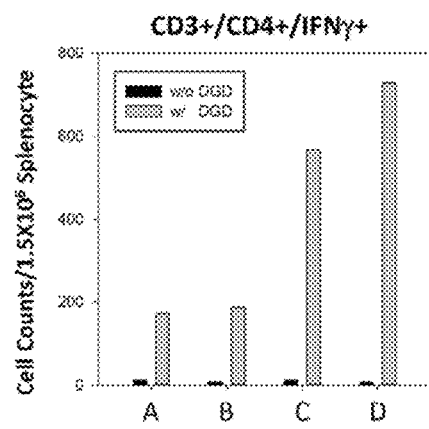
Figure 15H:
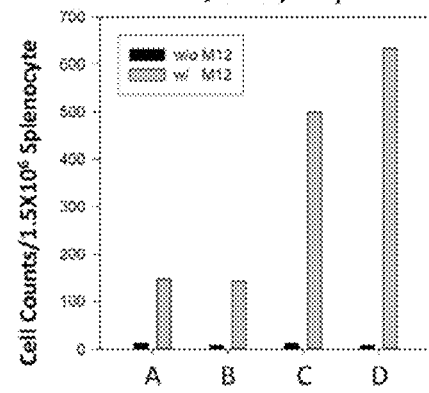
Figure 15I:
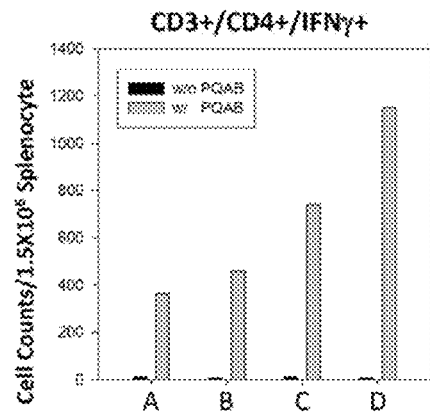
Figure 15J:
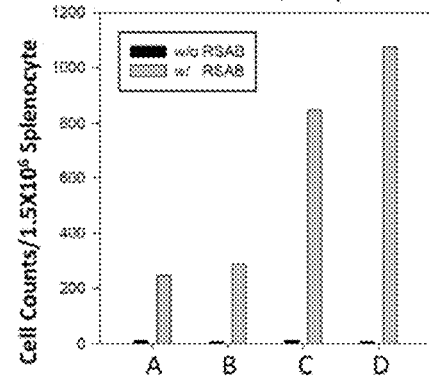

RAP1-CD28conv$PE_t$-E7-K3 Inhibits Growth of Tumors Induced by Human Papilloma Virus (HPV) Type 16 E7 Protein and Increases Survival Rate The effects of the fusion proteins $PE_{407}$-E7-K3 and RAP1-CD28conv$PE_t$-E7-K3 with or without an immune potentiator on tumor size and survival rate were examined. Mice were challenged with a higher dose of TC-01 cells ($3\times10^4$) via s.c. injection. Seven days after the challenge, mice were vaccinated via s.c. with placebo, $PE_{407}$-E7-K3 (100 μg/dose) or RAP1-CD28conv$PE_t$-E7-K3 (100 μg/dose) with the immune potentiator GPI-0100 or the protein absorbent aluminum phosphate once per week for 3 weeks (FIG. 9A). GPI-0100 is a Th1/CTL stimulating adjuvant (immune potentiator). The size of the tumors and the survival rate in each group were recorded (FIGS. 9B-C). When combined with the adjuvant GPI-0100, both $PE_t$-E7-K3 and RAP1-CD28conv$PE_t$-E7-K3 suppressed the tumor growth. Unexpectedly, it was discovered that the effect of RAP1-CD28conv$PE_t$-E7-K3 in inhibiting tumor growth was not dependent on the adjuvant. When combined with the absorbent aluminum phosphate rather than with the adjuvant GPI-0100, RAP1-CD28conv$PE_t$-E7-K3 could still significantly suppress the tumor growth with the same potency as that when combined with the immune potentiator GPI-0100 (FIG. 9B, unfilled triangle v. filed reverse triangle).

In contrast, the potency of $PE_{407}$-E7-K3 in suppressing the tumor growth depended on the adjuvant. When combined with the absorbent aluminum phosphate, $PE_{407}$-E7-K3 became less potent than that when combined with the immune potentiator GPI-0100 (FIG. 9B solid square v. unfilled circle).

On the other hand, mice administrated with RAP1-CD28conv$PE_t$-E7-K3 in combination with the immune potentiator GPI-0100 or the absorbent aluminum phosphate had a better survival rate than the groups vaccinated with $PE_{407}$-E7-K3 in combination with GPI-0100 or aluminum phosphate (FIG. 9C). This indicated that RAP1-CD28conv$PE_t$-E7-K3 could elicit Th1/CTL immune responses even without the immune potentiator GPI-0100. The results also indicated that the fusion protein RAP1-CD28conv$PE_t$-E7-K3 was superior to $PE_{407}$-E7-K3 as a vaccine for increasing the survival rate of the animals.

Example 5

Immunogenicity Assays

The immunogenicities of various vaccines were tested. Briefly, mice were divided into the following groups: HPV16 E7, HPV18 E7, HCV core, HBV HBx, PCV2 ORF2 and PRRSV (FIG. 13A). Each group was further divided into subgroups, and each subgroup was injected with either a placebo or a vaccine designed to target toward a certain antigen, or certain antigens, of a pathogen via s.c. once per week for 3 weeks (FIG. 13B). Except the vaccines targeted to PRRSV, each vaccine was composed of a single fusion protein and the absorbent aluminum phosphate, in which the single fusion protein contained at least an antigen of a pathogen. The antigen was either a full-length protein from a pathogen, or a non-full-length protein that contained at least one epitope of an antigen of a pathogen, or was a fusion peptide of two or more antigens, in which each of the antigens was selected from different proteins of a pathogen.

The immunization schedule, vaccines and dose are illustrated in FIGS. 13A-B. Briefly, mice were vaccinated once per week for 3 weeks with vaccines listed in FIG. 13A. All mice were sacrificed 7 days after the last immunization, and the spleens were harvested. Splenocytes were isolated and cultured in 6-well plate ($2 \times 10^7$ cells/2 ml/well) with 10 µg/ml of respective recombinant antigens of pathogens to stimulate the splenocytes in the presence of 1 µg/ml Golgi Plug (BD Pharmingen, San Diego, Calif.) at 37° C. for 16 hr.

The stimulated splenocytes were washed with FACScan buffer and the cell surface markers CD8a, CD4, and CD3 were stained with phycoerythrin-conjugated monoclonal rat anti-mouse CD8a, AF700-conjugated monoclonal rat anti-mouse CD4 and AF647-conjugated monoclonal rat anti-mouse CD3 antibodies. The cells were then permeabilized and fixed by Cytofix/Cytoperm kit according to the manufacturer's instructions (BD Pharmingen) Intracellular IFN-γ was stained with AF488-conjugated rat anti-mouse IFN-γ to measure the immune response and cytokine levels. Flow cytometry analyses were performed using Gallios flow cytometry with Kaluza analysis software (Beckman Coulter).

The following PRRSV vaccines were tested for immunogenicities: $PE_{407}$-PRRSV-K3, $RAP1-PE_{268-313}$-PRRSV-K3 or RAP1-CD28convPE$_t$-PRRSV-K3 vaccine. Each vaccine contained a mixture of four different fusion proteins, and each fusion protein contained a different antigen that is selected from the group consisting of DGD, M12, PQAB and RSAB (FIG. 13A). Vaccination of mice and stimulations of splenocytes were performed using similar method as described above. Briefly, all mice were sacrificed 7 days after the last immunization, and spleens were harvested. The splenocytes were isolated and cultured in 6-well plate ($2 \times 10^7$ cells/2 ml/well) with 10 µg/ml of the recombinant DGD M12, PQAB or RSAB antigens, separately, to stimulate the splenocytes in the presence of 1 µg/ml GolgiPlug (BD Pharmingen, San Diego, Calif.) at 37° C. for 16 hr.

The amino acid sequence of "DGD" (SEQ ID NO: 26) is as follows: RHHFTPSERQLCLSSIQTAFNQGAGT-CILSDSGRISYTVEFSLPTHHTVRLIRVTAPPS <u>ALDQVIRNALASPGSGGDLGEAIREQPEQARLALTL AAAESERFVRQGTGNDEAGAANADVVSLTCPVAA GECAGPADSGDALLERNYPTGAEFLGDGGDVRHH</u> FTPSERQLCLSSIQTAFNQGA GTCILSDSGRISYTVEF-SLPTHHTVRLIRVTAPPSA. DGD represents a fusion antigen of PRRSV ORF7 a.a. 64-a.a. 123 (boldface), linker (underlined) and ORF7 a.a. 64-a.a. 123 (boldface).

The term "M12" represents a antigen of PRRSV ORE1b a.a. 1046-a.a. 1210. Its amino acid sequence (SEQ ID NO: 27) is as follows:

NNKECTVAQALGNGDKFRATDKRVVDSLRAICADLEGSSSPLPKVAHNLG

FYFSPDLTQFAKLPIELAKIWPWSTQNNEKWPDRLVASLRPLDKYSRACI

GAGYNIVGPSVFLGTPGVVSYYLTKFVKGEAQVLPETVFSTGRIENDCRE

YLDDREREVAASLPH.

The amino acid sequence of "PQAB" (SEQ ID NO: 28) is as follows: GSSLDDFCYDSTAPQKVLLAFSITY <u>ASNDSSSHLQLIYNLTLCELNGTDWLANKFDWA</u>. PQAB represents a fusion antigen of PRRSV American strain ORF6 a.a. 2-a.a. 26 and ORE5 a.a. 31-a.a. 63 (underlined).

The amino acid sequence of RSAB is MGSLDDFCND-STAAQKLVLAFSITYTPI <u>FVAGGSSSTYQYIYNLTICELNGTDWLSNHFDWA</u> (SEQ ID NO: 29). The term "RSAB" represents a fusion antigen of PRRSV European strain ORF6 a.a. 2-28 and ORF5 a.a. 31-64 (underlined).

Example 6

The fragment of RAP1 domain 3 of the fusion protein RAP1-CD28convPE$_t$-E7-K3 is replaced by A2M minimum (SEQ ID NO: 6), HIV-Tat minimum (SEQ ID NO: 7) or HSPs minimum (SEQ ID NO: 8) to generate the fusion proteins A2M-CD28convPE$_t$-E7-K3, Tat-CD28convPE$_t$-E7-K3 and HSP-CD28convPE$_t$-E7-K3 vaccines, respectively. The TC-1 tumor suppression activity and cell mediated immune responses enhanced by these vaccines are examined using similar methods as described above. Table 1 shows SEQ ID NOs. of the components of various fusion proteins. Table 2 shows the fusion proteins tested for the effects on T cell-mediated immune responses in animals and the sequences of antigens.

TABLE 1

| Component | SEQ ID NO: | Length (residues) |
|---|---|---|
| hCD28 Core<br>TDIYFCKIEVMYPPPYLDNEKSNGTIIH | 1 | 28 |
| hCD28 Maximum<br>NCDGKLGNESVTFYLQNLYVNQTDIYFCKIEVMYPPPYLDNE<br>KSNGTIIHVKG | 2 | 53 |
| PE$_t$ Core (PE translocation domain core; a.a. 280-a.a. 313 of PE) | 3 | 34 |
| PE$_t$ Maximum (translocation domain maxi, a.a. 253-a.a. 364 of PE) | 4 | 112 |
| RAP1 Mini mum (domain III of RAP1) | 5 | 104 |

TABLE 1-continued

| Component | SEQ ID NO: | Length (residues) |
|---|---|---|
| A2M Minimum | 6 | 153 |
| HIV-Tat Minimum | 7 | 24 |
| HSPs Minimum, Heat shock 70 kDa protein (HSPs; *Homo sapiens*) | 8 | 641 |
| Minimum Pseudomonas exotoxin A (PE) binding domain Ia (an APC-binding domain, a.a. 1-a.a. 252 of PE) | 9 | 252 |
| Liner RXRXKR, ), in which "X" is any amino acid residue. | 15 | 6 |
| Full length PE (Exotoxin A mature form, *Pseudomonas aeruginosa*) | 10 | 613 |
| Full length RAP1 (*Homo sapiens* low density lipoprotein receptor-related protein associated protein 1, LRPAP1); Domain 1: a.a. 1-a.a 112; domain 2: a.a. 113-a.a. 218; domain 3: a.a. 219-a.a. 323. | 11 | 323 |
| Full length A2M (*Homo sapiens* alpha-2-macroglobulin receptor-associated protein precursor) | 12 | 357 |
| HIV-Tat (Human immunodeficiency virus 1) | 13 | 101 |
| KDEL | 14 | 4 |
| KKDLRDELKDEL | 16 | 12 |
| KKDELRDELKDEL | 17 | 13 |
| KKDELRVELKDEL | 18 | 13 |
| KDELKDELKDEL | 19 | 12 |
| $PE_{268-313}$ PLETFTRHRQPRGWEQLEQCGYPVQRLVALYLAARLSWNQV DQVIR | 20 | 46 |
| $CD28convPE_f$, $T^1D^2I^3Y^4F^5C^6K^7X^8E^9X^{10}X^{11}Y^{12}P^{13}P^{14}P^{15}Y^{16}X^{17}D^{18}N^{19}E^{20}K^{21}S^{22}N^{23}$ $G^{24}T^{25}I^{26}I^{27}H^{28}R^{29}X^{30}R^{31}X^{32}K^{33}R^{34}G^{35}W^{36}E^{37}Q^{38}L^{39}E^{40}Q^{41}C^{42}G^{43}Y^{44}$ $P^{45}V^{46}Q^{47}R^{48}L^{49}V^{50}A^{51}L^{52}Y^{53}L^{54}A^{55}A^{56}R^{57}L^{58}S^{59}W^{60}N^{61}Q^{62}V^{63}D^{64}Q^{65}$ $V^{66}I^{67}R^{68}$, wherein $(X)^8$ is I or L; $(X)^{10}$ is V, F or A, $(X)^{11}$ is M or L, $X^{17}$ is L or I, $(X)^{30, 32}$ is any amino acid residue. | 30 | 68 |
| CD28 consensus sequence $T^1D^2I^3Y^4F^5C^6K^7(X)^8E^9(X)^{10}(X)^{11}Y^{12}P^{13}P^{14}P^{15}Y^{16}X^{17}$ $D^{18}N^{19}E^{20}K^{21}S^{22}N^{23}G^{24}T^{25}I^{26}I^{27}H^{28}$, wherein $(X)^8$ is I or L; $(X)^{10}$ is V, F or A, $(X)^{11}$ is M or L, $X^{17}$ is L or I. | 31 | 28 |
| CD28 critical region $K^1(X)^2E^3(X)^4(X)^5Y^6P^7P^8P^9Y^{10}$, wherein $(X)^2$ is I or L; $(X)^4$ is V, F or A, $(X)^5$ is M or L. | 32 | 10 |

TABLE 2

| Fusion protein name | Antigen Name | Antigen SEQ ID NO: |
|---|---|---|
| $RAP1\text{-}CD28convPE_f\text{-}E7\text{-}K3$ | HPV16 E7 (full length) | 21 |
| $RAP1\text{-}CD28convPE_f\text{-}E7_{18}\text{-}K3$ | HPV18 E7 (full length) | 22 |
| $RAP1\text{-}CD28convPE_f\text{-}HCVc\text{-}K3$ | HCV core protein (full length) | 23 |
| $RAP1\text{-}CD28convPE_f\text{-}HBx\text{-}K3$ | HBV X protein (full length) | 24 |

TABLE 2-continued

| Fusion protein name | Antigen Name | Antigen SEQ ID NO: |
|---|---|---|
| RAP1-CD28convPE$_t$-PCV2-K3 | PCV2 ORF2 (a fragment of ORF2) | 25 |
| RAP1-CD28convPE$_t$-DGD-K3 | PRRSV nucleocapsid (a fusion antigen: ORF7 a.a. 64 - a.a. 123, linker and ORF7 a.a. 64- a.a. 123) | 26 |
| RAP1-CD28convPE$_t$-M12-K3 | PRRSV RNA-dependent RNA polymerase (ORf1b a.a. 1046-a.a. 1210) | 27 |
| RAP1-CD28convPE$_t$-PQAB-K3 | PRRSV American strain: a fusion antigen of ORF6 (a.a. 2-a.a. 26) and ORF5 (a.a. 31- a.a. 63) | 28 |
| RAP1-CD28convPE$_t$-RSAB-K3 | PRRSV European strain: a fusion antigen of ORF6 (a.a. 2-a.a. 28) and ORF5 (a.a. 31-a.a. 64) | 29 |

In the immunogenicity assays, antigen-specific cell-mediated immune responses induced by various vaccines were evaluated by measuring the numbers of CD3+/CD4+/IFNγ+ and CD3+/CD8+/IFNγ+ T cells in the splenocytes. The results indicated that the vaccine RAP1-CD28convPE$_t$-antigen-K3 can induce strong T cell responses. FIG. 14B shows the CD3+/CD4+/IFNγ+ T cell number and the CD3+/CD8+/IFNγ+ T cell number elicited by CD28convPE$_t$-E7$_{18}$-K3 were about 50 times and greater than 9 times of RAP1-K3, respectively.

The vaccine RAP1-CD28convPE$_t$-antigen-K3 is superior to PE$_{407}$-antigen-K3 in eliciting T cell-mediated immunogenicity. For example, FIG. 14A illustrates the CD3+/CD4+/IFNγ+ T cell number and the CD3+/CD8+/IFNγ+ T cell number elicited by CD28convPE$_t$-E7$_{16}$-K3 were about 5 times and 7 times of PE$_{407}$-E7$_{16}$-K3, respectively. This indicates that the vaccine RAP1-CD28convPE$_t$-E7-K3 had a better cell-mediated immunogenicity than PE$_{407}$-E7-K3.

A fusion protein comprising RAP1 domain III, the sensitizing signal CD28conv alone without the translocation peptide PE$_t$, antigen and an ER retention signal is sufficient in eliciting a strong antigen-specific T cell mediated immune responses when the antigen chosen comprises ten or greater than 10 epitopes. FIG. 14C illustrates the vaccine RAP1-CD28conv-HCVcore-K3 elicited T cell responses with the numbers of CD3+/CD4+/IFNγ+ and of CD3+/CD8+/IFNγ+ T cells being 20 times and 7.6 times of the placebo group, respectively. The antigen HCVcore contains 11 well-known MHC I epitopes.

It was unexpected that the ER retention signal is not essential for the fusion protein of the invention to elicit a strong cell-mediated immunogenicity. In other words, without the ER retention sequence, the fusion protein of the invention can still elicit strong T-cell responses. FIG. 14D illustrates that the numbers of CD3+/CD4+/IFNγ+ and CD3+/CD8+/IFNγ+ T cells elicited by RAP1-CD28convPE$_t$-HBx (without the ER retentions signal K3) were 7 times and 74 times of the placebo group.

In contrast, U.S. Pat. Nos. 7,378,100B2 and 7,335,361 show that the ER retention signal K3 is indispensable for PE-related fusion proteins (PE$_{407}$-antigen-K3) to elicit T cell responses.

It was also discovered that a fusion protein comprising RAP1 domain III, the translocation peptide PE$_{218-313}$ (without the sensitizing signal CD28conv), antigen and an ER retention signal is superior to a PE-related fusion protein without containing the RAP1 domain III. FIG. 15C-J illustrate the vaccine RAP1-PE$_{268-313}$-PRRSV-K3 elicited greater CD3+/CD4+/IFNγ+ and CD3+/CD8+/IFNγ+ T cell counts than the vaccine PE$_{407}$-PRRSV-K3.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A fusion protein comprising:
   (a) an antigen-presenting cell (APC)-binding domain or a CD91 receptor-binding domain, located at the N-terminus of the fusion protein;
   (b) a protein transduction domain, located at the C-terminus of the APC-binding domain or the CD91 receptor-binding domain, wherein the protein transduction domain is a fusion polypeptide consisting of:
   (1) a T cell sensitizing signal-transducing peptide consisting of 28-53 amino acid residues in length, comprising the amino acid sequence of SEQ ID NO: 31, in which $Xaa^8$ is I; $Xaa^{10}$ is V, F or A, $Xaa^{11}$ is M or L, $Xaa^{17}$ is L or I, being located at the N-terminus of the fusion polypeptide;

(2) a translocation peptide consisting of 34-112 amino acid residues in length, comprising an amino acid sequence that is at least 90% identical to SEQ ID NO: 3, 20 or 4; and
(3) a linker, comprising SEQ ID NO: 15 linking the T cell sensitizing signal-transducing peptide and the translocation peptide; and
(c) an antigen of a pathogen, located at the C-terminus of the protein transduction domain.

2. The fusion protein of claim 1, wherein the APC-binding domain or the CD91 receptor-binding domain is a polypeptide comprising an amino acid sequence that is at least 90% identical to the sequence selected from the group consisting of SEQ ID NOs: 5, 9, 6, 7, and 8.

3. The fusion protein of claim 1, further comprising an endoplasmic reticulum retention sequence located at the C-terminus of the fusion protein.

4. The fusion protein of claim 1, wherein the fusion protein is free of an endoplasmic reticulum retention sequence at C-terminus thereof if the antigen contains 10 or more epitopes.

5. A fusion protein consisting of:
(a) an antigen-presenting cell (APC)-binding domain or a CD91 receptor-binding domain, located at the N-terminus of the fusion protein;
(b) a protein transduction domain, located at the C-terminus of the APC-binding domain or the CD91 receptor-binding domain, wherein the protein transduction domain is selected from the group consisting of:
  (i) a T cell-sensitizing signal-transducing peptide consisting of 28-53 amino acid residues in length, comprising the amino acid sequence of SEQ ID NO: 31, in which $Xaa^8$ is I; $Xaa^{10}$ is V, F or A, $Xaa^{11}$ is M or L, $Xaa^{17}$ is L or I; and
  (ii) a translocation peptide of 34-46 amino acid residues in length, comprising an amino acid sequence that is at least 90% identical to SEQ ID NO: 3 or 20; and
(c) an antigen of a pathogen, located at the C-terminus of the protein transduction domain:
wherein:
the APC-binding domain or the CD91 receptor-binding domain is free of the amino acid sequence of *Pseudomonas* exotoxin A (PE) binding domain I if the protein transduction domain is the translocation peptide.

6. The fusion protein of claim 5, wherein the protein transduction domain is the T cell-sensitizing signal-transducing peptide.

7. The fusion protein of claim 5, wherein the protein transduction domain is the translocation peptide.

8. The fusion protein of claim 1, wherein the protein transduction domain comprises the sequence of SEQ ID NO: 30.

9. A fusion protein consisting of:
(a) an antigen-presenting cell (APC)-binding domain or a CD91 receptor-binding domain, located at the N-terminus of the fusion protein;
(b) a protein transduction domain, located at the C-terminus of the APC-binding domain or the CD91 receptor-binding domain, wherein the protein transduction domain is selected from the group consisting of:
  (i) a T cell-sensitizing signal-transducing peptide consisting of 28-53 amino acid residues in length, comprising the amino acid sequence of SEQ ID NO: 31, in which $Xaa^8$ is I; $Xaa^{10}$ is V, F or A, $Xaa^{11}$ is M or L, $Xaa^{17}$ is L or I; and
  (ii) a translocation peptide of 34-46 amino acid residues in length, comprising an amino acid sequence that is at least 90% identical to SEQ ID NO: 3 or 20; and;
(c) an antigen of a pathogen, located at the C-terminus of the protein transduction domain; and
(d) an endoplasmic reticulum retention sequence located at the C-terminus of the fusion protein.

10. The fusion protein of claim 1, wherein the APC-binding domain or the CD91 receptor-binding domain is a polypeptide comprising an amino acid sequence selected from the group consisting of SEQ ID NOs: 5, 9, 6, 7, and 8.

11. The fusion protein of claim 1, wherein the T cell sensitizing signal-transducing peptide comprises the amino acid sequence of SEQ ID NO: 1.

12. The fusion protein of claim 1, wherein the translocation peptide comprises the amino acid sequence of SEQ ID NO: 3.

13. A method for inducing enhanced pathogen antigen-specific T cell responses, comprising:
administering a vaccine composition comprising a therapeutically effective amount of the fusion protein of claim 1 to a subject in need thereof, and thereby inducing enhanced pathogen antigen-specific T cell responses.

14. The fusion protein of claim 1, wherein the pathogen is at least one selected from the group consisting of Human Papillomavirus (HPV), Porcine Reproductive and Respiratory Syndrome Virus (PRRSV), Human immuno-deficient Virus (HIV-1), flu virus, dengue virus, Hepatitis C virus (HCV), Hepatitis B virus (HBV) and Porcine Circovirus 2 (PCV2).

15. A fusion protein comprising:
(a) an antigen-presenting cell (APC)-binding domain or a CD91 receptor-binding domain, located at the N-terminus of the fusion protein;
(b) a protein transduction domain, located at the C-terminus of the APC-binding domain or the CD91 receptor-binding domain, wherein the protein transduction domain is a fusion polypeptide consisting of:
  (1) a T cell sensitizing signal-transducing peptide of 28 amino acid residues in length, consisting of the amino acid sequence of SEQ ID NO: 31, in which $Xaa^8$ is I or L; $Xaa^{10}$ is V, F or A, $Xaa^{11}$ is M or L, $Xaa^{17}$ is L or I, being located at the N-terminus of the fusion polypeptide;
  (2) a translocation peptide consisting of 34-112 amino acid residues in length, comprising an amino acid sequence that is at least 90% identical to SEQ ID NO: 3, 20 or 4; and
  (3) a linker, comprising SEQ ID NO: 15 linking the T cell sensitizing signal-transducing peptide and the translocation peptide; and
(c) an antigen of a pathogen, located at the C-terminus of the protein transduction domain.

* * * * *

SEQUENCE LISTING

```
<160> NUMBER OF SEQ ID NOS: 43

<210> SEQ ID NO 1
<211> LENGTH: 28
<212> TYPE: PRT
<213> ORGANISM: Artificial Sequence
<220> FEATURE:
<223> OTHER INFORMATION: hCD28 Core

<400> SEQUENCE: 1

Thr Asp Ile Tyr Phe Cys Lys Ile Glu Val Met Tyr Pro Pro Pro Tyr
1               5                   10                  15

Leu Asp Asn Glu Lys Ser Asn Gly Thr Ile Ile His
            20                  25
```

<210> SEQ ID NO 2
<211> LENGTH: 53
<212> TYPE: PRT
<213> ORGANISM: Artificial Sequence
<220> FEATURE:
<223> OTHER INFORMATION: hCD28 Maximum

<400> SEQUENCE: 2

Asn Cys Asp Gly Lys Leu Gly Asn Glu Ser Val Thr Phe Tyr Leu Gln
1               5                   10                  15

Asn Leu Tyr Val Asn Gln Thr Asp Ile Tyr Phe Cys Lys Ile Glu Val
            20                  25                  30

Met Tyr Pro Pro Pro Tyr Leu Asp Asn Glu Lys Ser Asn Gly Thr Ile
        35                  40                  45

Ile His Val Lys Gly
    50

<210> SEQ ID NO 3
<211> LENGTH: 34
<212> TYPE: PRT
<213> ORGANISM: Artificial Sequence
<220> FEATURE:
<223> OTHER INFORMATION: PEt Core

<400> SEQUENCE: 3

Gly Trp Glu Gln Leu Glu Gln Cys Gly Tyr Pro Val Gln Arg Leu Val
1               5                   10                  15

Ala Leu Tyr Leu Ala Ala Arg Leu Ser Trp Asn Gln Val Asp Gln Val
            20                  25                  30

Ile Arg

<210> SEQ ID NO 4
<211> LENGTH: 112
<212> TYPE: PRT
<213> ORGANISM: Artificial Sequence
<220> FEATURE:
<223> OTHER INFORMATION: PEt Maximum

<400> SEQUENCE: 4

Gly Gly Ser Leu Ala Ala Leu Thr Ala His Gln Ala Cys His Leu Pro
1               5                   10                  15

Leu Glu Thr Phe Thr Arg His Arg Gln Pro Arg Gly Trp Glu Gln Leu
            20                  25                  30

Glu Gln Cys Gly Tyr Pro Val Gln Arg Leu Val Ala Leu Tyr Leu Ala
        35                  40                  45

Ala Arg Leu Ser Trp Asn Gln Val Asp Gln Val Ile Arg Asn Ala Leu
    50                  55                  60

Ala Ser Pro Gly Ser Gly Asp Leu Gly Glu Ala Ile Arg Glu Gln
65                  70                  75                  80

Pro Glu Gln Ala Arg Leu Ala Leu Thr Leu Ala Ala Ala Glu Ser Glu
            85                  90                  95

Arg Phe Val Arg Gln Gly Thr Gly Asn Asp Glu Ala Gly Ala Ala Asn
        100                 105                 110

<210> SEQ ID NO 5
<211> LENGTH: 104
<212> TYPE: PRT
<213> ORGANISM: Artificial Sequence
<220> FEATURE:
<223> OTHER INFORMATION: RAP1 Minimum

<400> SEQUENCE: 5

Ala Glu Phe Glu Glu Pro Arg Val Ile Asp Leu Trp Asp Leu Ala Gln
1               5                   10                  15

Ser Ala Asn Leu Thr Asp Lys Glu Leu Glu Ala Phe Arg Glu Glu Leu
            20                  25                  30

Lys His Phe Glu Ala Lys Ile Glu Lys His Asn His Tyr Gln Lys Gln
        35                  40                  45

Leu Glu Ile Ala His Lys Leu Arg His Ala Glu Ser Val Gly Asp
    50                  55                  60

Gly Glu Arg Val Ser Arg Ser Arg Glu Lys His Ala Leu Leu Glu Gly
65                  70                  75                  80

Arg Thr Lys Glu Leu Gly Tyr Thr Val Lys Lys His Leu Gln Asp Leu
                85                  90                  95

Ser Gly Arg Ile Ser Arg Ala Arg
            100

<210> SEQ ID NO 6
<211> LENGTH: 153
<212> TYPE: PRT
<213> ORGANISM: Artificial Sequence
<220> FEATURE:
<223> OTHER INFORMATION: A2M Minimum

<400> SEQUENCE: 6

Val Tyr Leu Gln Thr Ser Leu Lys Tyr Asn Ile Leu Pro Glu Lys Glu
1               5                   10                  15

Glu Phe Pro Phe Ala Leu Gly Val Gln Thr Leu Pro Gln Thr Cys Asp
            20                  25                  30

Glu Pro Lys Ala His Thr Ser Phe Gln Ile Ser Leu Ser Val Ser Tyr
        35                  40                  45

Thr Gly Ser Arg Ser Ala Ser Asn Met Ala Ile Val Asp Val Lys Met
    50                  55                  60

Val Ser Gly Phe Ile Pro Leu Lys Pro Thr Val Lys Met Leu Glu Arg
65                  70                  75                  80

Ser Asn His Val Ser Arg Thr Glu Val Ser Ser Asn His Val Leu Ile
                85                  90                  95

Tyr Leu Asp Lys Val Ser Asn Gln Thr Leu Ser Leu Phe Phe Thr Val
            100                 105                 110

Leu Gln Asp Val Pro Val Arg Asp Leu Lys Pro Ala Ile Val Lys Val
        115                 120                 125

Tyr Asp Tyr Tyr Glu Thr Asp Glu Phe Ala Ile Ala Glu Tyr Asn Ala
    130                 135                 140

Pro Cys Ser Lys Asp Leu Gly Asn Ala
145                 150

<210> SEQ ID NO 7
<211> LENGTH: 24
<212> TYPE: PRT
<213> ORGANISM: Artificial Sequence
<220> FEATURE:
<223> OTHER INFORMATION: HIV-Tat Minimum

<400> SEQUENCE: 7

Arg Gly Asp Pro Thr Gly Gln Glu Glu Ser Lys Glu Lys Val Glu Lys
1               5                   10                  15

Glu Thr Val Val Asp Pro Val Thr
            20

```
<210> SEQ ID NO 8
<211> LENGTH: 641
<212> TYPE: PRT
<213> ORGANISM: Artificial Sequence
<220> FEATURE:
<223> OTHER INFORMATION: HSPs Minimum

<400> SEQUENCE: 8

Met Ala Lys Ala Ala Ile Gly Ile Asp Leu Gly Thr Thr Tyr Ser
1               5                   10                  15

Cys Val Gly Val Phe Gln His Gly Lys Val Glu Ile Ile Ala Asn Asp
                20                  25                  30

Gln Gly Asn Arg Thr Thr Pro Ser Tyr Val Ala Phe Thr Asp Thr Glu
            35                  40                  45

Arg Leu Ile Gly Asp Ala Ala Lys Asn Gln Val Ala Leu Asn Pro Gln
        50                  55                  60

Asn Thr Val Phe Asp Ala Lys Arg Leu Ile Gly Arg Lys Phe Gly Asp
65                  70                  75                  80

Pro Val Val Gln Ser Asp Met Lys His Trp Pro Phe Gln Val Ile Asn
                85                  90                  95

Asp Gly Asp Lys Pro Lys Val Gln Val Ser Tyr Lys Gly Glu Thr Lys
            100                 105                 110

Ala Phe Tyr Pro Glu Glu Ile Ser Ser Met Val Leu Thr Lys Met Lys
        115                 120                 125

Glu Ile Ala Glu Ala Tyr Leu Gly Tyr Pro Val Thr Asn Ala Val Ile
    130                 135                 140

Thr Val Pro Ala Tyr Phe Asn Asp Ser Gln Arg Gln Ala Thr Lys Asp
145                 150                 155                 160

Ala Gly Val Ile Ala Gly Leu Asn Val Leu Arg Ile Ile Asn Glu Pro
                165                 170                 175

Thr Ala Ala Ala Ile Ala Tyr Gly Leu Asp Arg Thr Gly Lys Gly Glu
            180                 185                 190

Arg Asn Val Leu Ile Phe Asp Leu Gly Gly Gly Thr Phe Asp Val Ser
        195                 200                 205

Ile Leu Thr Ile Asp Asp Gly Ile Phe Glu Val Lys Ala Thr Ala Gly
    210                 215                 220

Asp Thr His Leu Gly Gly Glu Asp Phe Asp Asn Arg Leu Val Asn His
225                 230                 235                 240

Phe Val Glu Glu Phe Lys Arg Lys His Lys Lys Asp Ile Ser Gln Asn
                245                 250                 255

Lys Arg Ala Val Arg Arg Leu Arg Thr Ala Cys Glu Arg Ala Lys Arg
            260                 265                 270

Thr Leu Ser Ser Ser Thr Gln Ala Ser Leu Glu Ile Asp Ser Leu Phe
        275                 280                 285

Glu Gly Ile Asp Phe Tyr Thr Ser Ile Thr Arg Ala Arg Phe Glu Glu
    290                 295                 300

Leu Cys Ser Asp Leu Phe Arg Ser Thr Leu Glu Pro Val Glu Lys Ala
305                 310                 315                 320

Leu Arg Asp Ala Lys Leu Asp Lys Ala Gln Ile His Asp Leu Val Leu
                325                 330                 335

Val Gly Gly Ser Thr Arg Ile Pro Lys Val Gln Lys Leu Leu Gln Asp
            340                 345                 350

Phe Phe Asn Gly Arg Asp Leu Asn Lys Ser Ile Asn Pro Asp Glu Ala
        355                 360                 365
```

```
Val Ala Tyr Gly Ala Ala Val Gln Ala Ile Leu Met Gly Asp Lys
    370             375             380

Ser Glu Asn Val Gln Asp Leu Leu Leu Asp Val Ala Pro Leu Ser
385             390             395             400

Leu Gly Leu Glu Thr Ala Gly Gly Val Met Thr Ala Leu Ile Lys Arg
                405             410             415

Asn Ser Thr Ile Pro Thr Lys Gln Thr Gln Ile Phe Thr Thr Tyr Ser
                420             425             430

Asp Asn Gln Pro Gly Val Leu Ile Gln Val Tyr Glu Gly Glu Arg Ala
            435             440             445

Met Thr Lys Asp Asn Asn Leu Leu Gly Arg Phe Glu Leu Ser Gly Ile
450             455             460

Pro Pro Ala Pro Arg Gly Val Pro Gln Ile Glu Val Thr Phe Asp Ile
465             470             475             480

Asp Ala Asn Gly Ile Leu Asn Val Thr Ala Thr Asp Lys Ser Thr Gly
                485             490             495

Lys Ala Asn Lys Ile Thr Ile Thr Asn Asp Lys Gly Arg Leu Ser Lys
            500             505             510

Glu Glu Ile Glu Arg Met Val Gln Glu Ala Glu Lys Tyr Lys Ala Glu
            515             520             525

Asp Glu Val Gln Arg Glu Arg Val Ser Ala Lys Asn Ala Leu Glu Ser
530             535             540

Tyr Ala Phe Asn Met Lys Ser Ala Val Glu Asp Glu Gly Leu Lys Gly
545             550             555             560

Lys Ile Ser Glu Ala Asp Lys Lys Val Leu Asp Lys Cys Gln Glu
                565             570             575

Val Ile Ser Trp Leu Asp Ala Asn Thr Leu Ala Glu Lys Asp Glu Phe
            580             585             590

Glu His Lys Arg Lys Glu Leu Glu Gln Val Cys Asn Pro Ile Ile Ser
            595             600             605

Gly Leu Tyr Gln Gly Ala Gly Gly Pro Gly Pro Gly Gly Phe Gly Ala
            610             615             620

Gln Gly Pro Lys Gly Gly Ser Gly Ser Gly Pro Thr Ile Glu Glu Val
625             630             635             640

Asp

<210> SEQ ID NO 9
<211> LENGTH: 252
<212> TYPE: PRT
<213> ORGANISM: Pseudomonas aeruginosa

<400> SEQUENCE: 9

Ala Glu Glu Ala Phe Asp Leu Trp Asn Glu Cys Ala Lys Ala Cys Val
1               5               10              15

Leu Asp Leu Lys Asp Gly Val Arg Ser Ser Arg Met Ser Val Asp Pro
            20              25              30

Ala Ile Ala Asp Thr Asn Gly Gln Gly Val Leu His Tyr Ser Met Val
        35              40              45

Leu Glu Gly Gly Asn Asp Ala Leu Lys Leu Ala Ile Asp Asn Ala Leu
50              55              60

Ser Ile Thr Ser Asp Gly Leu Thr Ile Arg Leu Glu Gly Gly Val Glu
65              70              75              80

Pro Asn Lys Pro Val Arg Tyr Ser Tyr Thr Arg Gln Ala Arg Gly Ser
                85              90              95
```

-continued

```
Trp Ser Leu Asn Trp Leu Val Pro Ile Gly His Glu Lys Pro Ser Asn
            100                 105                 110
Ile Lys Val Phe Ile His Glu Leu Asn Ala Gly Asn Gln Leu Ser His
        115                 120                 125
Met Ser Pro Ile Tyr Thr Ile Glu Met Gly Asp Glu Leu Leu Ala Lys
    130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Thr Gln Pro Arg Arg Glu Lys Arg Trp Ser Glu Trp Ala Ser
            180                 185                 190
Gly Lys Val Leu Cys Leu Leu Asp Pro Leu Asp Gly Val Tyr Asn Tyr
        195                 200                 205
Leu Ala Gln Gln Arg Cys Asn Leu Asp Asp Thr Trp Glu Gly Lys Ile
    210                 215                 220
Tyr Arg Val Leu Ala Gly Asn Pro Ala Lys His Asp Leu Asp Ile Lys
225                 230                 235                 240
Pro Thr Val Ile Ser His Arg Leu His Phe Pro Glu
                245                 250

<210> SEQ ID NO 10
<211> LENGTH: 613
<212> TYPE: PRT
<213> ORGANISM: Pseudomonas aeruginosa

<400> SEQUENCE: 10

Ala Glu Glu Ala Phe Asp Leu Trp Asn Glu Cys Ala Lys Ala Cys Val
1               5                   10                  15
Leu Asp Leu Lys Asp Gly Val Arg Ser Ser Arg Met Ser Val Asp Pro
            20                  25                  30
Ala Ile Ala Asp Thr Asn Gly Gln Gly Val Leu His Tyr Ser Met Val
        35                  40                  45
Leu Glu Gly Gly Asn Asp Ala Leu Lys Leu Ala Ile Asp Asn Ala Leu
    50                  55                  60
Ser Ile Thr Ser Asp Gly Leu Thr Ile Arg Leu Glu Gly Gly Val Glu
65                  70                  75                  80
Pro Asn Lys Pro Val Arg Tyr Ser Tyr Thr Arg Gln Ala Arg Gly Ser
                85                  90                  95
Trp Ser Leu Asn Trp Leu Val Pro Ile Gly His Glu Lys Pro Ser Asn
            100                 105                 110
Ile Lys Val Phe Ile His Glu Leu Asn Ala Gly Asn Gln Leu Ser His
        115                 120                 125
Met Ser Pro Ile Tyr Thr Ile Glu Met Gly Asp Glu Leu Leu Ala Lys
    130                 135                 140
Leu Ala Arg Asp Ala Thr Phe Phe Val Arg Ala His Glu Ser Asn Glu
145                 150                 155                 160
Met Gln Pro Thr Leu Ala Ile Ser His Ala Gly Val Ser Val Val Met
                165                 170                 175
Ala Gln Thr Gln Pro Arg Arg Glu Lys Arg Trp Ser Glu Trp Ala Ser
            180                 185                 190
Gly Lys Val Leu Cys Leu Leu Asp Pro Leu Asp Gly Val Tyr Asn Tyr
        195                 200                 205
Leu Ala Gln Gln Arg Cys Asn Leu Asp Asp Thr Trp Glu Gly Lys Ile
    210                 215                 220
```

Tyr Arg Val Leu Ala Gly Asn Pro Ala Lys His Asp Leu Asp Ile Lys
225                 230                 235                 240

Pro Thr Val Ile Ser His Arg Leu His Phe Pro Glu Gly Gly Ser Leu
            245                 250                 255

Ala Ala Leu Thr Ala His Gln Ala Cys His Leu Pro Leu Glu Thr Phe
        260                 265                 270

Thr Arg His Arg Gln Pro Arg Gly Trp Glu Gln Leu Glu Gln Cys Gly
    275                 280                 285

Tyr Pro Val Gln Arg Leu Val Ala Leu Tyr Leu Ala Ala Arg Leu Ser
290                 295                 300

Trp Asn Gln Val Asp Val Ile Arg Asn Ala Leu Ala Ser Pro Gly
305                 310                 315                 320

Ser Gly Gly Asp Leu Gly Glu Ala Ile Arg Glu Gln Pro Glu Gln Ala
                325                 330                 335

Arg Leu Ala Leu Thr Leu Ala Ala Ala Glu Ser Glu Arg Phe Val Arg
            340                 345                 350

Gln Gly Thr Gly Asn Asp Glu Ala Gly Ala Ala Asn Ala Asp Val Val
        355                 360                 365

Ser Leu Thr Cys Pro Val Ala Ala Gly Glu Cys Ala Gly Pro Ala Asp
    370                 375                 380

Ser Gly Asp Ala Leu Leu Glu Arg Asn Tyr Pro Thr Gly Ala Glu Phe
385                 390                 395                 400

Leu Gly Asp Gly Gly Asp Val Ser Phe Ser Thr Arg Gly Thr Gln Asn
                405                 410                 415

Trp Thr Val Glu Arg Leu Leu Gln Ala His Arg Gln Leu Glu Glu Arg
            420                 425                 430

Gly Tyr Val Phe Val Gly Tyr His Gly Thr Phe Leu Glu Ala Ala Gln
        435                 440                 445

Ser Ile Val Phe Gly Gly Val Arg Ala Arg Ser Gln Asp Leu Asp Ala
    450                 455                 460

Ile Trp Arg Gly Phe Tyr Ile Ala Gly Asp Pro Ala Leu Ala Tyr Gly
465                 470                 475                 480

Tyr Ala Gln Asp Gln Glu Pro Asp Ala Arg Gly Arg Ile Arg Asn Gly
                485                 490                 495

Ala Leu Leu Arg Val Tyr Val Pro Arg Ser Ser Leu Pro Gly Phe Tyr
            500                 505                 510

Arg Thr Ser Leu Thr Leu Ala Ala Pro Glu Ala Ala Gly Glu Val Glu
        515                 520                 525

Arg Leu Ile Gly His Pro Leu Pro Leu Arg Leu Asp Ala Ile Thr Gly
    530                 535                 540

Pro Glu Glu Glu Gly Gly Arg Leu Glu Thr Ile Leu Gly Trp Pro Leu
545                 550                 555                 560

Ala Glu Arg Thr Val Val Ile Pro Ser Ala Ile Pro Thr Asp Pro Arg
                565                 570                 575

Asn Val Gly Gly Asp Leu Asp Pro Ser Ser Ile Pro Asp Lys Glu Gln
            580                 585                 590

Ala Ile Ser Ala Leu Pro Asp Tyr Ala Ser Gln Pro Gly Lys Pro Pro
        595                 600                 605

Arg Glu Asp Leu Lys
    610

<210> SEQ ID NO 11
<211> LENGTH: 323

```
<212> TYPE: PRT
<213> ORGANISM: Homo sapiens

<400> SEQUENCE: 11

Tyr Ser Arg Glu Lys Asn Gln Pro Lys Pro Ser Pro Lys Arg Glu Ser
1               5                   10                  15

Gly Glu Glu Phe Arg Met Glu Lys Leu Asn Gln Leu Trp Glu Lys Ala
            20                  25                  30

Gln Arg Leu His Leu Pro Pro Val Arg Leu Ala Glu Leu His Ala Asp
        35                  40                  45

Leu Lys Ile Gln Glu Arg Asp Glu Leu Ala Trp Lys Lys Leu Lys Leu
    50                  55                  60

Asp Gly Leu Asp Glu Asp Gly Glu Lys Glu Ala Arg Leu Ile Arg Asn
65                  70                  75                  80

Leu Asn Val Ile Leu Ala Lys Tyr Gly Leu Asp Gly Lys Lys Asp Ala
                85                  90                  95

Arg Gln Val Thr Ser Asn Ser Leu Ser Gly Thr Gln Glu Asp Gly Leu
            100                 105                 110

Asp Asp Pro Arg Leu Glu Lys Leu Trp His Lys Ala Lys Thr Ser Gly
        115                 120                 125

Lys Phe Ser Gly Glu Glu Leu Asp Lys Leu Trp Arg Glu Phe Leu His
    130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
                165                 170                 175

Asp Ile Lys Gly Ser Val Leu His Ser Arg His Thr Glu Leu Lys Glu
            180                 185                 190

Lys Leu Arg Ser Ile Asn Gln Gly Leu Asp Arg Leu Arg Arg Val Ser
        195                 200                 205

His Gln Gly Tyr Ser Thr Glu Ala Glu Phe Glu Glu Pro Arg Val Ile
    210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
                245                 250                 255

His Asn His Tyr Gln Lys Gln Leu Glu Ile Ala His Glu Lys Leu Arg
            260                 265                 270

His Ala Glu Ser Val Gly Asp Gly Glu Arg Val Ser Arg Ser Arg Glu
        275                 280                 285

Lys His Ala Leu Leu Glu Gly Arg Thr Lys Glu Leu Gly Tyr Thr Val
    290                 295                 300

Lys Lys His Leu Gln Asp Leu Ser Gly Arg Ile Ser Arg Ala Arg His
305                 310                 315                 320

Asn Glu Leu

<210> SEQ ID NO 12
<211> LENGTH: 357
<212> TYPE: PRT
<213> ORGANISM: Homo sapiens

<400> SEQUENCE: 12

Met Ala Pro Arg Arg Val Arg Ser Phe Leu Arg Gly Leu Pro Ala Leu
1               5                   10                  15

Leu Leu Leu Leu Leu Phe Leu Gly Pro Trp Pro Ala Ala Ser His Gly
```

```
                20                  25                  30
Gly Lys Tyr Ser Arg Glu Lys Asn Gln Pro Lys Pro Ser Pro Lys Arg
            35                  40                  45
Glu Ser Gly Glu Glu Phe Arg Met Glu Lys Leu Asn Gln Leu Trp Glu
        50                  55                  60
Lys Ala Gln Arg Leu His Leu Pro Pro Val Arg Leu Ala Glu Leu His
65                  70                  75                  80
Ala Asp Leu Lys Ile Gln Glu Arg Asp Glu Leu Ala Trp Lys Lys Leu
                85                  90                  95
Lys Leu Asp Gly Leu Asp Glu Asp Gly Glu Lys Glu Ala Arg Leu Ile
            100                 105                 110
Arg Asn Leu Asn Val Ile Leu Ala Lys Tyr Gly Leu Asp Gly Lys Lys
        115                 120                 125
Asp Ala Arg Gln Val Thr Ser Asn Ser Leu Ser Gly Thr Gln Glu Asp
        130                 135                 140
Gly Leu Asp Asp Pro Arg Leu Glu Lys Leu Trp His Lys Ala Lys Thr
145                 150                 155                 160
Ser Gly Lys Phe Ser Gly Glu Glu Leu Asp Lys Leu Trp Arg Glu Phe
                165                 170                 175
Leu His His Lys Glu Lys Val His Glu Tyr Asn Val Leu Leu Glu Thr
            180                 185                 190
Leu Ser Arg Thr Glu Glu Ile His Glu Asn Val Ile Ser Pro Ser Asp
        195                 200                 205
Leu Ser Asp Ile Lys Gly Ser Val Leu His Ser Arg His Thr Glu Leu
        210                 215                 220
Lys Glu Lys Leu Arg Ser Ile Asn Gln Gly Leu Asp Arg Leu Arg Arg
225                 230                 235                 240
Val Ser His Gln Gly Tyr Ser Thr Glu Ala Glu Phe Glu Glu Pro Arg
                245                 250                 255
Val Ile Asp Leu Trp Asp Leu Ala Gln Ser Ala Asn Leu Thr Asp Lys
            260                 265                 270
Glu Leu Glu Ala Phe Arg Glu Glu Leu Lys His Phe Glu Ala Lys Ile
        275                 280                 285
Glu Lys His Asn His Tyr Gln Lys Gln Leu Glu Ile Ala His Glu Lys
        290                 295                 300
Leu Arg His Ala Glu Ser Val Gly Asp Gly Glu Arg Val Ser Arg Ser
305                 310                 315                 320
Arg Glu Lys His Ala Leu Leu Glu Gly Arg Thr Lys Glu Leu Gly Tyr
                325                 330                 335
Thr Val Lys Lys His Leu Gln Asp Leu Ser Gly Arg Ile Ser Arg Ala
            340                 345                 350
Arg His Asn Glu Leu
        355

<210> SEQ ID NO 13
<211> LENGTH: 101
<212> TYPE: PRT
<213> ORGANISM: Human immunodeficiency virus

<400> SEQUENCE: 13

Met Glu Pro Val Asp Pro Arg Leu Glu Pro Trp Lys His Pro Gly Ser
1               5                   10                  15
Gln Pro Lys Thr Pro Cys Thr Lys Cys Tyr Cys Lys Lys Cys Cys Leu
            20                  25                  30
```

```
His Cys Gln Val Cys Phe Met Thr Lys Gly Leu Gly Ile Ser Tyr Gly
            35                  40                  45

Arg Lys Lys Arg Arg Gln Arg Arg Ala Pro Gln Asp Asn Lys Asn
 50                  55                  60

His Gln Val Ser Leu Ser Lys Gln Pro Thr Ser Arg Ala Arg Gly Asp
 65                  70                  75                  80

Pro Thr Gly Gln Glu Glu Ser Lys Glu Lys Val Glu Lys Thr Val
                85                  90                  95

Val Asp Pro Val Thr
            100

<210> SEQ ID NO 14
<211> LENGTH: 4
<212> TYPE: PRT
<213> ORGANISM: Artificial Sequence
<220> FEATURE:
<223> OTHER INFORMATION: ER retention sequence

<400> SEQUENCE: 14

Lys Asp Glu Leu
1

<210> SEQ ID NO 15
<211> LENGTH: 6
<212> TYPE: PRT
<213> ORGANISM: Artificial Sequence
<220> FEATURE:
<223> OTHER INFORMATION: Linker of CD28-PEt
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 15

Arg Xaa Arg Xaa Lys Arg
1               5

<210> SEQ ID NO 16
<211> LENGTH: 12
<212> TYPE: PRT
<213> ORGANISM: Artificial Sequence
<220> FEATURE:
<223> OTHER INFORMATION: ER retention sequence

<400> SEQUENCE: 16

Lys Lys Asp Leu Arg Asp Glu Leu Lys Asp Glu Leu
1               5                  10

<210> SEQ ID NO 17
<211> LENGTH: 13
<212> TYPE: PRT
<213> ORGANISM: Artificial Sequence
<220> FEATURE:
<223> OTHER INFORMATION: ER retention sequence

<400> SEQUENCE: 17

Lys Lys Asp Glu Leu Arg Asp Glu Leu Lys Asp Glu Leu
1               5                  10

<210> SEQ ID NO 18
<211> LENGTH: 13
<212> TYPE: PRT
```

```
<213> ORGANISM: Artificial Sequence
<220> FEATURE:
<223> OTHER INFORMATION: ER retention sequence

<400> SEQUENCE: 18

Lys Lys Asp Glu Leu Arg Val Glu Leu Lys Asp Glu Leu
1               5                   10

<210> SEQ ID NO 19
<211> LENGTH: 12
<212> TYPE: PRT
<213> ORGANISM: Artificial Sequence
<220> FEATURE:
<223> OTHER INFORMATION: ER retention sequence

<400> SEQUENCE: 19

Lys Asp Glu Leu Lys Asp Glu Leu Lys Asp Glu Leu
1               5                   10

<210> SEQ ID NO 20
<211> LENGTH: 46
<212> TYPE: PRT
<213> ORGANISM: Pseudomonas aeruginosa

<400> SEQUENCE: 20

Pro Leu Glu Thr Phe Thr Arg His Arg Gln Pro Arg Gly Trp Glu Gln
1               5                   10                  15

Leu Glu Gln Cys Gly Tyr Pro Val Gln Arg Leu Val Ala Leu Tyr Leu
                20                  25                  30

Ala Ala Arg Leu Ser Trp Asn Gln Val Asp Gln Val Ile Arg
            35                  40                  45

<210> SEQ ID NO 21
<211> LENGTH: 98
<212> TYPE: PRT
<213> ORGANISM: Human papillomavirus type 16

<400> SEQUENCE: 21

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
                20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                  70                  75                  80

Asp Leu Leu Met Gly Thr Leu Gly Ile Val Cys Pro Ile Cys Ser Gln
                85                  90                  95

Lys Pro

<210> SEQ ID NO 22
<211> LENGTH: 105
<212> TYPE: PRT
<213> ORGANISM: Human papillomavirus type 18

<400> SEQUENCE: 22

Met His Gly Pro Lys Ala Thr Leu Gln Asp Ile Val Leu His Leu Glu
1               5                   10                  15

Pro Gln Asn Glu Ile Pro Val Asp Leu Leu Cys His Glu Gln Leu Ser
```

```
                    20                  25                  30
Asp Ser Glu Glu Asn Asp Glu Ile Asp Gly Val Asn His Gln His
            35                  40                  45

Leu Pro Ala Arg Arg Ala Glu Pro Gln Arg His Thr Met Leu Cys Met
    50                  55                  60

Cys Cys Lys Cys Glu Ala Arg Ile Lys Leu Val Val Glu Ser Ser Ala
65                  70                  75                  80

Asp Asp Leu Arg Ala Phe Gln Gln Leu Phe Leu Asn Thr Leu Ser Phe
                85                  90                  95

Val Cys Pro Trp Cys Ala Ser Gln Gln
            100                 105

<210> SEQ ID NO 23
<211> LENGTH: 190
<212> TYPE: PRT
<213> ORGANISM: Hepatitis C virus

<400> SEQUENCE: 23

Met Ser Thr Asn Pro Lys Pro Gln Arg Lys Thr Lys Arg Asn Thr Asn
1               5                   10                  15

Arg Arg Pro Gln Asp Val Lys Phe Pro Gly Gly Gly Gln Ile Val Gly
                20                  25                  30

Gly Val Tyr Leu Leu Pro Arg Arg Gly Pro Arg Leu Gly Val Arg Ala
            35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Met Gly Trp Ala Gly Trp
                85                  90                  95

Leu Leu Ser Pro Arg Gly Ser Arg Pro Asn Trp Gly Pro Thr Asp Pro
            100                 105                 110

Arg Arg Arg Ser Arg Asn Leu Gly Lys Val Ile Asp Thr Leu Thr Cys
    115                 120                 125

Gly Phe Ala Asp Leu Met Gly Tyr Ile Pro Leu Val Gly Ala Pro Leu
130                 135                 140

Gly Gly Val Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Thr Pro Ala Ser
            180                 185                 190

<210> SEQ ID NO 24
<211> LENGTH: 154
<212> TYPE: PRT
<213> ORGANISM: Hepatitis B virus

<400> SEQUENCE: 24

Met Ala Ala Arg Met Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
                20                  25                  30

Pro Leu Gly Ala Leu Pro Pro Ser Ala Ser Ala Val Pro Ala Asp
            35                  40                  45

His Gly Ser His Leu Ser Leu Arg Gly Leu Pro Val Cys Ser Phe Ser
```

```
                    50                  55                  60
Ser Ala Gly Pro Cys Ala Leu Arg Phe Thr Ser Ala Arg Arg Met Glu
 65                  70                  75                  80

Thr Thr Val Asn Ala Pro Trp Ser Leu Pro Thr Val Leu His Lys Arg
                 85                  90                  95

Thr Ile Gly Leu Ser Gly Arg Ser Met Thr Trp Ile Glu Glu Tyr Ile
                100                 105                 110

Lys Asp Cys Val Phe Lys Asp Trp Glu Glu Leu Gly Glu Glu Ile Arg
                115                 120                 125

Leu Lys Val Phe Val Leu Gly Gly Cys Arg His Lys Leu Val Cys Ser
                130                 135                 140

Pro Ala Pro Cys Asn Phe Phe Thr Ser Ala
145                 150

<210> SEQ ID NO 25
<211> LENGTH: 192
<212> TYPE: PRT
<213> ORGANISM: Porcine circovirus

<400> SEQUENCE: 25

Asn Gly Ile Phe Asn Thr Arg Leu Ser Arg Thr Phe Gly Tyr Thr Ile
  1               5                  10                  15

Lys Arg Thr Thr Val Lys Thr Pro Ser Trp Ala Val Asp Met Met Arg
                 20                  25                  30

Phe Asn Ile Asn Asp Phe Leu Pro Pro Gly Gly Gly Ser Asn Pro Arg
                 35                  40                  45

Ser Val Pro Phe Glu Tyr Tyr Ser Ile Ser Lys Val Lys Val Glu Phe
 50                  55                  60

Trp Pro Cys Ser Pro Ile Thr Gln Gly Asp Ser Gly Val Gly Ser Ser
 65                  70                  75                  80

Ala Val Ile Leu Asp Asp Asn Phe Val Thr Lys Ala Thr Ala Leu Thr
                 85                  90                  95

Tyr Asp Pro Tyr Val Asn Tyr Ser Ser Arg His Thr Ile Thr Gln Pro
                100                 105                 110

Phe Ser Tyr His Ser Arg Tyr Phe Thr Pro Lys Pro Val Leu Asp Ser
                115                 120                 125

Thr Ile Asp Tyr Phe Gln Pro Asn Asn Lys Arg Asn Gln Leu Trp Leu
                130                 135                 140

Arg Leu Gln Thr Ala Gly Asn Val Asp His Val Gly Leu Gly Thr Ala
145                 150                 155                 160

Phe Glu Asn Ser Ile Tyr Asp Gln Glu Tyr Asn Ile Arg Val Thr Met
                165                 170                 175

Tyr Val Gln Phe Arg Glu Phe Asn Leu Lys Asp Pro Pro Leu Asn Pro
                180                 185                 190

<210> SEQ ID NO 26
<211> LENGTH: 220
<212> TYPE: PRT
<213> ORGANISM: Porcine reproductive and respiratory syndrome virus

<400> SEQUENCE: 26

Arg His His Phe Thr Pro Ser Glu Arg Gln Leu Cys Leu Ser Ser Ile
  1               5                  10                  15

Gln Thr Ala Phe Asn Gln Gly Ala Gly Thr Cys Ile Leu Ser Asp Ser
                 20                  25                  30

Gly Arg Ile Ser Tyr Thr Val Glu Phe Ser Leu Pro Thr His His Thr
```

-continued

```
                35                  40                  45
Val Arg Leu Ile Arg Val Thr Ala Pro Pro Ser Ala Leu Asp Gln Val
 50                  55                  60

Ile Arg Asn Ala Leu Ala Ser Pro Gly Ser Gly Asp Leu Gly Glu
 65                  70                  75                  80

Ala Ile Arg Glu Gln Pro Glu Gln Ala Arg Leu Ala Leu Thr Leu Ala
                 85                  90                  95

Ala Ala Glu Ser Glu Arg Phe Val Arg Gln Gly Thr Gly Asn Asp Glu
                100                 105                 110

Ala Gly Ala Ala Asn Ala Asp Val Val Ser Leu Thr Cys Pro Val Ala
                115                 120                 125

Ala Gly Glu Cys Ala Gly Pro Ala Asp Ser Gly Asp Ala Leu Leu Glu
                130                 135                 140

Arg Asn Tyr Pro Thr Gly Ala Glu Phe Leu Gly Asp Gly Asp Val
145                 150                 155                 160

Arg His His Phe Thr Pro Ser Glu Arg Gln Leu Cys Leu Ser Ser Ile
                165                 170                 175

Gln Thr Ala Phe Asn Gln Gly Ala Gly Thr Cys Ile Leu Ser Asp Ser
                180                 185                 190

Gly Arg Ile Ser Tyr Thr Val Glu Phe Ser Leu Pro Thr His His Thr
                195                 200                 205

Val Arg Leu Ile Arg Val Thr Ala Pro Pro Ser Ala
                210                 215                 220
```

<210> SEQ ID NO 27
<211> LENGTH: 165
<212> TYPE: PRT
<213> ORGANISM: Porcine reproductive and respiratory syndrome virus

<400> SEQUENCE: 27

```
Asn Asn Lys Glu Cys Thr Val Ala Gln Ala Leu Gly Asn Gly Asp Lys
 1               5                  10                  15

Phe Arg Ala Thr Asp Lys Arg Val Val Asp Ser Leu Arg Ala Ile Cys
                20                  25                  30

Ala Asp Leu Glu Gly Ser Ser Ser Pro Leu Pro Lys Val Ala His Asn
                35                  40                  45

Leu Gly Phe Tyr Phe Ser Pro Asp Leu Thr Gln Phe Ala Lys Leu Pro
 50                  55                  60

Ile Glu Leu Asp Pro His Trp Pro Val Val Ser Thr Gln Asn Asn Glu
 65                  70                  75                  80

Lys Trp Pro Asp Arg Leu Val Ala Ser Leu Arg Pro Leu Asp Lys Tyr
                 85                  90                  95

Ser Arg Ala Cys Ile Gly Ala Gly Tyr Met Val Gly Pro Ser Val Phe
                100                 105                 110

Leu Gly Thr Pro Gly Val Val Ser Tyr Tyr Leu Thr Lys Phe Val Lys
                115                 120                 125

Gly Glu Ala Gln Val Leu Pro Glu Thr Val Phe Ser Thr Gly Arg Ile
                130                 135                 140

Glu Val Asp Cys Arg Glu Tyr Leu Asp Asp Arg Glu Arg Glu Val Ala
145                 150                 155                 160

Ala Ser Leu Pro His
                165
```

<210> SEQ ID NO 28
<211> LENGTH: 58

```
<212> TYPE: PRT
<213> ORGANISM: Porcine reproductive and respiratory syndrome virus

<400> SEQUENCE: 28

Gly Ser Ser Leu Asp Asp Phe Cys Tyr Asp Ser Thr Ala Pro Gln Lys
1               5                   10                  15

Val Leu Leu Ala Phe Ser Ile Thr Tyr Ala Ser Asn Asp Ser Ser Ser
            20                  25                  30

His Leu Gln Leu Ile Tyr Asn Leu Thr Leu Cys Glu Leu Asn Gly Thr
        35                  40                  45

Asp Trp Leu Ala Asn Lys Phe Asp Trp Ala
    50                  55

<210> SEQ ID NO 29
<211> LENGTH: 62
<212> TYPE: PRT
<213> ORGANISM: Porcine reproductive and respiratory syndrome virus

<400> SEQUENCE: 29

Met Gly Ser Leu Asp Asp Phe Cys Asn Asp Ser Thr Ala Ala Gln Lys
1               5                   10                  15

Leu Val Leu Ala Phe Ser Ile Thr Tyr Thr Pro Ile Phe Val Ala Gly
            20                  25                  30

Gly Ser Ser Ser Thr Tyr Gln Tyr Ile Tyr Asn Leu Thr Ile Cys Glu
        35                  40                  45

Leu Asn Gly Thr Asp Trp Leu Ser Asn His Phe Asp Trp Ala
    50                  55                  60

<210> SEQ ID NO 30
<211> LENGTH: 68
<212> TYPE: PRT
<213> ORGANISM: Artificial Sequence
<220> FEATURE:
<223> OTHER INFORMATION: CD28-PEt
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid

<400> SEQUENCE: 30

Thr Asp Ile Tyr Phe Cys Lys Xaa Glu Xaa Xaa Tyr Pro Pro Pro Tyr
1               5                   10                  15

Xaa Asp Asn Glu Lys Ser Asn Gly Thr Ile Ile His Arg Xaa Arg Xaa
            20                  25                  30

Lys Arg Gly Trp Glu Gln Leu Glu Gln Cys Gly Tyr Pro Val Gln Arg
        35                  40                  45

Leu Val Ala Leu Tyr Leu Ala Leu Arg Leu Ser Trp Asn Gln Val Asp
    50                  55                  60
```

Gln Val Ile Arg
65

<210> SEQ ID NO 31
<211> LENGTH: 28
<212> TYPE: PRT
<213> ORGANISM: Artificial Sequence
<220> FEATURE:
<223> OTHER INFORMATION: CD28 consensus sequence
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 31

Thr Asp Ile Tyr Phe Cys Lys Xaa Glu Xaa Xaa Tyr Pro Pro Pro Tyr
1               5                   10                  15

Xaa Asp Asn Glu Lys Ser Asn Gly Thr Ile Ile His
            20                  25

<210> SEQ ID NO 32
<211> LENGTH: 10
<212> TYPE: PRT
<213> ORGANISM: Artificial Sequence
<220> FEATURE:
<223> OTHER INFORMATION: CD28 critical region
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 32

Lys Xaa Glu Xaa Xaa Tyr Pro Pro Pro Tyr
1               5                   10

<210> SEQ ID NO 33
<211> LENGTH: 33
<212> TYPE: PRT
<213> ORGANISM: Homo sapiens

<400> SEQUENCE: 33

Gln Asn Leu Tyr Val Asn Gln Thr Asp Ile Tyr Phe Cys Lys Ile Glu
1               5                   10                  15

Val Met Tyr Pro Pro Pro Tyr Leu Asp Asn Glu Lys Ser Asn Gly Thr
            20                  25                  30

Ile

<210> SEQ ID NO 34
<211> LENGTH: 33
<212> TYPE: PRT
<213> ORGANISM: Rattus norvegicus

<400> SEQUENCE: 34

Trp Asn Leu Asp Val Asn His Thr Asp Ile Tyr Phe Cys Lys Ile Glu
1               5                   10                  15

```
Val Met Tyr Pro Pro Tyr Leu Asp Asn Glu Lys Ser Asn Gly Thr
            20                  25                  30

Ile

<210> SEQ ID NO 35
<211> LENGTH: 33
<212> TYPE: PRT
<213> ORGANISM: Mus musculus

<400> SEQUENCE: 35

Trp Asn Leu His Val Asn His Thr Asp Ile Tyr Phe Cys Lys Ile Glu
1               5                   10                  15

Phe Met Tyr Pro Pro Pro Tyr Leu Asp Asn Glu Arg Ser Asn Gly Thr
            20                  25                  30

Ile

<210> SEQ ID NO 36
<211> LENGTH: 33
<212> TYPE: PRT
<213> ORGANISM: Oryctolagus cuniculus

<400> SEQUENCE: 36

Lys Asn Leu Tyr Val Asn Gln Thr Asp Ile Tyr Phe Cys Lys Ile Glu
1               5                   10                  15

Val Met Tyr Pro Pro Pro Tyr Leu Asp Asn Glu Lys Ser Asn Gly Thr
            20                  25                  30

Ile

<210> SEQ ID NO 37
<211> LENGTH: 33
<212> TYPE: PRT
<213> ORGANISM: Sus scrofa

<400> SEQUENCE: 37

Arg Asn Leu His Val Asn Gln Thr Asp Ile Tyr Phe Cys Lys Ile Glu
1               5                   10                  15

Val Leu Tyr Pro Pro Pro Tyr Ile Asp Asn Glu Lys Ser Asn Gly Thr
            20                  25                  30

Ile

<210> SEQ ID NO 38
<211> LENGTH: 33
<212> TYPE: PRT
<213> ORGANISM: Bos taurus

<400> SEQUENCE: 38

Gln Asp Leu Tyr Val Asn Gln Thr Asp Ile Tyr Phe Cys Lys Leu Glu
1               5                   10                  15

Val Leu Tyr Pro Pro Pro Tyr Ile Asp Asn Glu Lys Ser Asn Gly Thr
            20                  25                  30

Ile

<210> SEQ ID NO 39
<211> LENGTH: 33
<212> TYPE: PRT
<213> ORGANISM: Ovis aries

<400> SEQUENCE: 39

Gln Asp Leu Tyr Val Asn Gln Thr Asp Ile Tyr Phe Cys Lys Leu Glu
1               5                   10                  15
```

```
Val Leu Tyr Pro Pro Tyr Ile Asp Asn Glu Lys Ser Asn Gly Thr
            20                  25                  30
Ile

<210> SEQ ID NO 40
<211> LENGTH: 33
<212> TYPE: PRT
<213> ORGANISM: Canis familiaris

<400> SEQUENCE: 40

Arg Asn Leu Phe Val Asn Gln Thr Asp Ile Tyr Phe Cys Lys Ile Glu
1               5                   10                  15

Val Met Tyr Pro Pro Tyr Ile Gly Asn Glu Lys Ser Asn Gly Thr
            20                  25                  30
Ile

<210> SEQ ID NO 41
<211> LENGTH: 33
<212> TYPE: PRT
<213> ORGANISM: Equus caballus

<400> SEQUENCE: 41

Trp Asn Leu Tyr Val Asn Gln Thr Asp Ile Tyr Phe Cys Lys Ile Glu
1               5                   10                  15

Val Met Tyr Pro Pro Tyr Ile Asp Asn Glu Lys Ser Asn Gly Thr
            20                  25                  30
Ile

<210> SEQ ID NO 42
<211> LENGTH: 33
<212> TYPE: PRT
<213> ORGANISM: Meleagris gallopavo

<400> SEQUENCE: 42

Arg Asn Met Thr Ala Ser Gln Thr Asp Ile Tyr Phe Cys Lys Ile Glu
1               5                   10                  15

Ala Met Tyr Pro Pro Pro Tyr Val Tyr Asn Glu Lys Ser Asn Gly Thr
            20                  25                  30
Val

<210> SEQ ID NO 43
<211> LENGTH: 32
<212> TYPE: PRT
<213> ORGANISM: Artificial Sequence
<220> FEATURE:
<223> OTHER INFORMATION: NLYVNQTDIYFCKIEVMYPPPYIDNEKSNGTI

<400> SEQUENCE: 43

Asn Leu Tyr Val Asn Gln Thr Asp Ile Tyr Phe Cys Lys Ile Glu Val
1               5                   10                  15

Met Tyr Pro Pro Pro Tyr Ile Asp Asn Glu Lys Ser Asn Gly Thr Ile
            20                  25                  30
```